United States Patent
Sekiya et al.

(10) Patent No.: US 8,479,561 B2
(45) Date of Patent: Jul. 9, 2013

(54) GAS CONCENTRATION DETECTION SENSOR

(75) Inventors: Takayuki Sekiya, Nissin (JP); Kei Kosaka, Nagoya (JP); Shodai Hirata, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 167 days.

(21) Appl. No.: 13/109,352

(22) Filed: May 17, 2011

(65) Prior Publication Data

US 2011/0283775 A1    Nov. 24, 2011

(30) Foreign Application Priority Data

May 18, 2010 (JP) ................... 2010-114527
May 16, 2011 (JP) ................... 2011-109373

(51) Int. Cl.
*G01N 7/00* (2006.01)
(52) U.S. Cl.
USPC .......................................... 73/31.05; 73/23.31
(58) Field of Classification Search
USPC .......... 73/23.2, 31.05, 114.71, 114.73, 23.31, 73/30.01, 23.4, 24.06, 25.05, 29.05, 30.04; 204/426, 428
See application file for complete search history.

(56) References Cited

U.S. PATENT DOCUMENTS

| 6,348,141 | B1 | 2/2002 | Kato et al. | |
| 7,901,556 | B2 * | 3/2011 | Yamada | 204/428 |
| 2005/0178187 | A1 * | 8/2005 | Nakagawa | 73/31.05 |
| 2008/0016948 | A1 * | 1/2008 | Yamada | 73/31.05 |
| 2008/0028831 | A1 * | 2/2008 | Nakashima et al. | 73/31.05 |
| 2008/0209984 | A1 * | 9/2008 | Yamada | 73/31.05 |

FOREIGN PATENT DOCUMENTS

JP    2000-304719    11/2000

* cited by examiner

*Primary Examiner* — Daniel Larkin
*Assistant Examiner* — Jamar Ray
(74) *Attorney, Agent, or Firm* — Burr & Brown

(57) ABSTRACT

First outer gas apertures 144a are arranged in a first corner 144b such that the outer opening plane of each first outer gas aperture 144a forms an angle of 45 degrees with a bottom face of a step element 145 and the outer opening plane forms an angle of 90 degrees with an inner circumferential face of the first outer gas aperture 144a. Second outer gas apertures are arranged in a second corner 146b such that the outer opening plane of each second outer gas aperture 146a forms an angle of 45 degrees with a bottom face of an edge section 146 and the outer opening plane forms an angle of 90 degrees with an inner circumferential face of the second outer gas aperture 146a. This structure prevents water from adhering to a sensor element 110 and thereby enhances the response of a gas sensor 110.

7 Claims, 23 Drawing Sheets (a)

(b)

(a)

(b)

(a)

(b)

(a)

(b)

GAS CONCENTRATION DETECTION SENSOR

BACKGROUND OF THE INVENTION

1. Field of the Invention

The present invention relates to a gas concentration detection sensor.

2. Description or the Related Art

Gas concentration detection sensors have been known to detect the concentration of a selected gas, for example, NOx or oxygen, included in an object gas, such as emission or exhaust gas from an automobile. In the gas concentration detection sensors, the presence of water generated at an engine start time and adhering to a sensor element may lower the temperature of the sensor element and cause cracking in the sensor element. One proposed measure for preventing the occurrence of cracking provides a protective cover to cover over the sensor element. For example, in a gas sensor disclosed in Patent Document 1, as one example of the protective cover, a protector of a double-layered structure is provided around an outer circumference of an edge section of the sensor element.

Patent Document 1: JP 2000-304719 A (FIG. 11)

SUMMARY OF THE INVENTION

The protective cover has an aperture to introduce the object gas into the sensor element. Water may enter the protection cover through the aperture and adhere to the sensor element. To more effectively prevent the adhesion of water, the number of protective covers may be increased to two or three, alternatively, a flow path for the object gas inside the protective cover may be complicated. In such a case, the time the object gas takes to reach the sensor element increases, thus reducing gas concentration detection response. A protective cover has accordingly been demanded to enhance both of the prevention of water adhesion to the sensor element and the response of the gas concentration detection sensor.

By taking into account the issue discussed above, an object of the present invention is to provide a gas concentration detection sensor having the structure of preventing the adhesion of water to a sensor element and enhancing gas concentration detection response.

In order to attain at least part of the object above, a gas concentration detection sensor of the present invention is constructed as follows.

The gas concentration detection sensor of the invention includes: a sensor element that detects concentration of a selected gas included in an object gas; a bottomed cylindrical inner protection cover that covers over a free end of the sensor element; an outer protection cover having a larger diameter than a diameter of the inner protection cover and having a side face and a bottom face; a plurality of outer gas apertures arranged in a boundary portion between the side face and the bottom face of the outer protection cover; and an inner gas aperture positioned closer to a base end of the sensor element than the outer gas apertures, the inner gas aperture allowing the object gas to flow inside and outside the inner protection cover. An angle formed by the outer opening plane of each outer gas aperture and the bottom face of the outer protection cover is in a range of 10 degrees to 80 degrees.

In the gas concentration detection sensor according to one aspect of the invention, the outer gas apertures are arranged in the boundary portion between the side face and the bottom face of the outer protection cover and the angle formed by the outer opening plane of each outer gas aperture and the bottom face of the outer protection cover is in the range of 10 degrees to 80 degrees. This structure effectively facilitates the discharge of water in the outer protection cover therefrom to the outside through the outer gas apertures, compared with a structure in which the apertures are arranged around the side face and a structure in which the angle formed by the outer opening plane of each outer gas aperture and the bottom face of the outer protection cover is not in the range of 10 degrees to 80 degrees. This structure therefore prevents water from entering the inner protection cover and adhering to the sensor element. The outer gas apertures allow the object gas entering the outer protection cover through the outer gas apertures to flow toward the base end of the sensor element. This structure effectively facilitates the arrival of the object gas entering through the outer gas apertures at the inner gas aperture, compared with the structure in which the outer gas apertures are arranged around the side face of the outer protection cover and the structure in which the angle formed by the outer opening plane of each outer gas aperture and the bottom face of the outer protection cover is not in the range of 10 degrees to 80 degrees. This structure therefore reduces the time to replace a gas in the protection covers with the object gas, thus enhancing the response of the gas concentration detection sensor. The above-described structure prevents the adhesion of water to the sensor element and thereby enhances the gas concentration detection response. The total area of the outer gas apertures may be 6 to 13 mm$^2$.

In one preferable embodiment of the gas concentration detection sensor of the invention, the outer protection cover has a cylindrical stem section, a bottomed cylindrical edge section having a smaller diameter than a diameter of the stem section, and a step element connecting the stem section with the edge section, the outer gas apertures include a plurality of first outer gas apertures arranged in a first corner, serving as a boundary portion between a side face of the stem section of the outer protection cover and a bottom face of the step element of the outer protection cover, and a plurality of second outer gas apertures arranged in a second corner, serving as a boundary portion between a side face and a bottom face of the edge section of the outer protection cover, the inner gas aperture is positioned closer to the base end of the sensor element than the first outer gas apertures, and the sensor further includes a first gas chamber defined by the stem section and the step element of the outer protection cover and the inner protection cover such that the first gas chamber communicates with the inside of the inner protection cover through the inner gas aperture, a second gas chamber defined by the edge section of the outer protection cover and the inner protection cover such that the second gas chamber does not directly communicate with the first gas chamber, and a gas passing aperture that allows the object gas to flow between the second gas chamber and the inside of the inner protection cover. The arrangement of this embodiment also facilitates the discharge of water in the outer protection cover therefrom to the outside through the first and second outer gas apertures, thus preventing water from entering the inner protection cover and adhering to the sensor element. The first outer gas apertures allow the object gas entering the first gas chamber through the first outer gas apertures to flow toward the base end of the sensor element. The inner gas aperture is positioned closer to the base end of the sensor element than the first outer gas apertures. This arrangement reduces the time to replace a gas in the protection covers with the object gas, thus enhancing the response of the gas concentration detection sensor.

In another preferable embodiment of the gas concentration detection sensor including the first outer gas apertures and the second outer gas apertures, the total area of openings of the second outer gas apertures is larger than that of the first outer gas apertures. In the arrangement where the total area of the second outer gas apertures is larger than that of the first outer gas apertures, an amount of object gas entering through the second outer gas apertures is larger than that through the first outer gas apertures in a transient state caused, for example, when the flow rate of the object gas sharply increases. This results in the occurrence or a pressure acting from the second gas chamber into the inner protection cover and further acting from the inner protection cover into the first gas chamber in the transient state. The pressure pushes water out of the first gas chamber through the first outer gas apertures. The arrangement more effectively prevents the adhesion of water to the sensor element.

In a state other than the transient state, since the edge section of the outer protection cover is bottomed cylindrical, the flow of the object gas along the bottom face of the edge section causes the object gas in the second gas chamber to be sucked out through the second outer gas apertures. The total area of the second outer gas apertures larger than that of the first outer gas apertures increases a force to suck out the object gas. This arrangement facilitates the discharge of the object gas entering the first gas chamber through the first outer gas apertures to the outside via the inner protection cover and the second gas chamber, thus enhancing the response of the gas concentration detection sensor.

In another preferable embodiment of the gas concentration detection sensor of the invention, the gas passing aperture is disposed in a position other than extensions of the second outer gas apertures. If water enters through the second outer gas apertures in the transient state, this arrangement lowers the probability that the water reaches the inside of the inner protection cover. This arrangement therefore more effectively prevents the adhesion of water to the sensor element. The extension of each second outer gas aperture is a region where when light having directivity is virtually applied from a direction along the central axis of the second outer gas aperture, the light impinges on the inner protection cover.

In another preferable embodiment of the gas concentration detection sensor in which the total area of openings of the second outer gas apertures is larger than that of the first outer gas apertures, the first outer gas apertures have the same area of opening, the second outer gas apertures have the same area of opening, and the area of opening of each second outer gas aperture is equal to or larger than that of each first outer gas aperture.

In another preferable embodiment of the gas concentration detection sensor including the first outer gas apertures and the second outer gas apertures, the first outer gas apertures are three or more apertures arranged at equal intervals and the second outer gas apertures are three or more apertures arranged at equal intervals. In this arrangement, even if the object gas flows from any direction on an outer circumferential face of the outer protection cover, at least one first outer gas aperture and at least one second outer gas aperture facing the upstream side of the object gas are surely present and at least one first outer gas aperture and at least one second outer gas aperture facing the downstream side of the object gas are surely present. This arrangement ensures that the object gas is introduced into the outer protection cover and the inner protection cover to perform gas concentration detection by the sensor element, irrespective of the attachment orientation of the gas concentration detection sensor.

In another preferable embodiment of the gas concentration detection sensor including the first outer gas apertures and the second outer gas apertures, the gas passing aperture is disposed in a boundary portion between a side face and a bottom face of the inner protection cover and an angle formed by the outer opening plane of the gas passing aperture and the bottom face of the inner protection cover is in a range of 10 degrees to 80 degrees. In this arrangement, the gas passing aperture allows the object gas entering the second gas chamber from the inside of the inner protection cover to flow toward the second outer gas apertures. This arrangement more effectively facilitates the arrival of the object gas, entering the second gas chamber from the inside of the inner protection cover, at the second outer gas apertures, compared with a structure in which the gas passing aperture is disposed on the side face or the bottom face of the inner protection cover and a structure in which the angle formed by the outer opening plane of the gas passing aperture and the bottom face of the inner protection cover is not in the range of 10 degrees to 80 degrees. This arrangement therefore reduces the time the object gas takes to reach the outside via the second gas chamber and thereby enhances the response of the gas concentration detection sensor.

BRIEF DESCRIPTION OF DRAWINGS

FIG. 4 is an enlarged partial sectional view of a portion including a first outer gas aperture 144a.

FIG. 5 is an enlarged partial sectional view of a portion including second outer gas apertures 146a and gas passing apertures 138a.

FIG. 14 is an explanatory view of positions of gas passing apertures 241a.

DETAILED DESCRIPTION OF THE INVENTION

Figure 1:
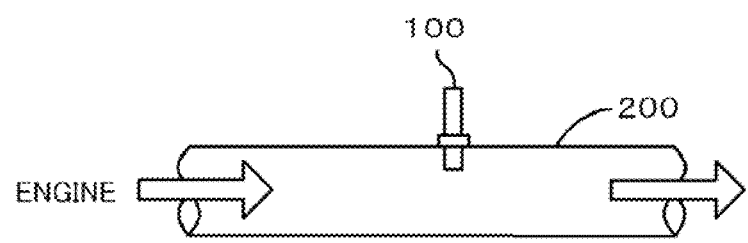
FIG. 1 is an explanatory diagrammatic view of a gas concentration detection sensor 100 attached to piping 200.
Figure 2:
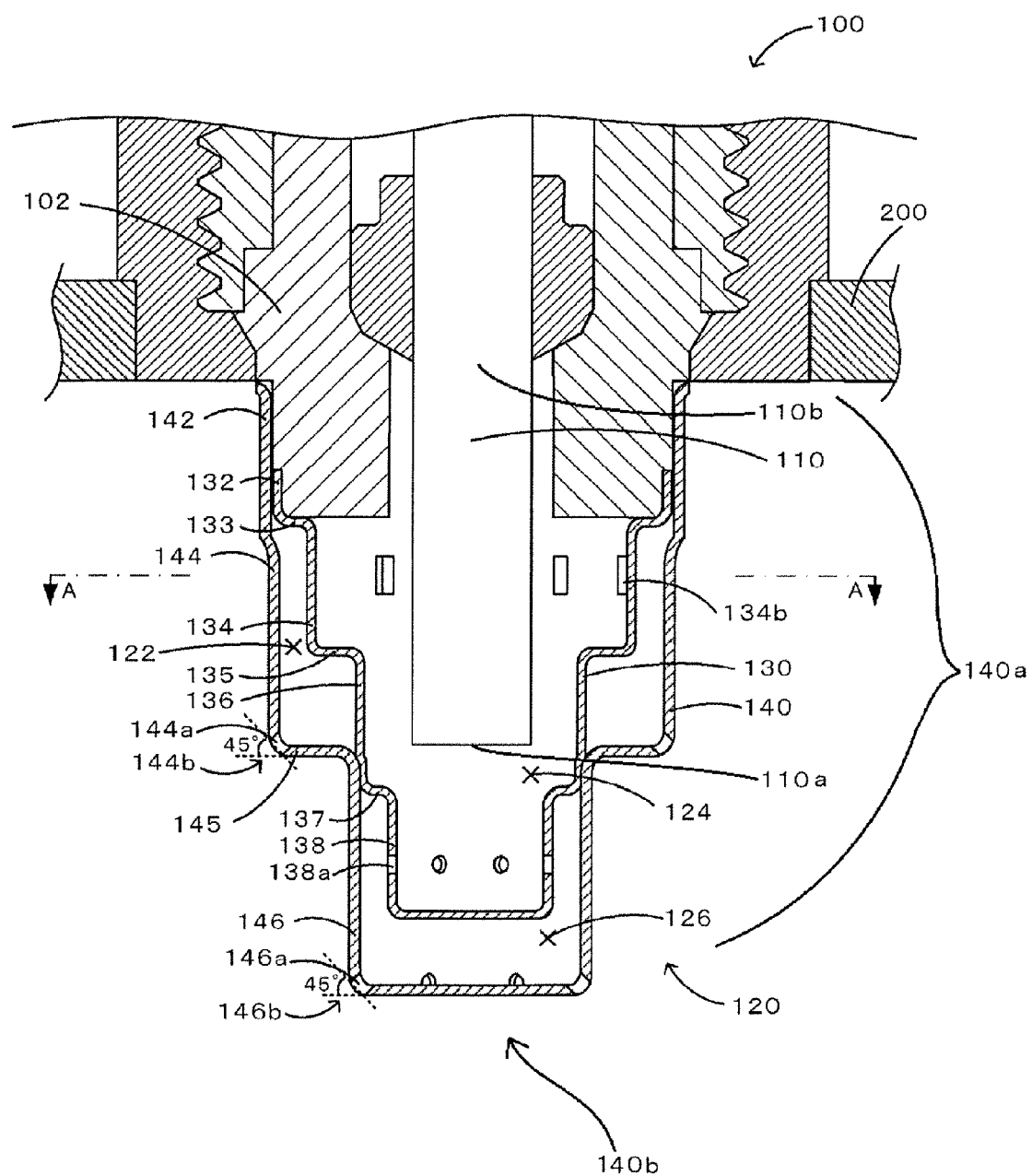
FIG. 2 is a vertical sectional view of the structure of the gas concentration detection sensor 100.
Figure 3:
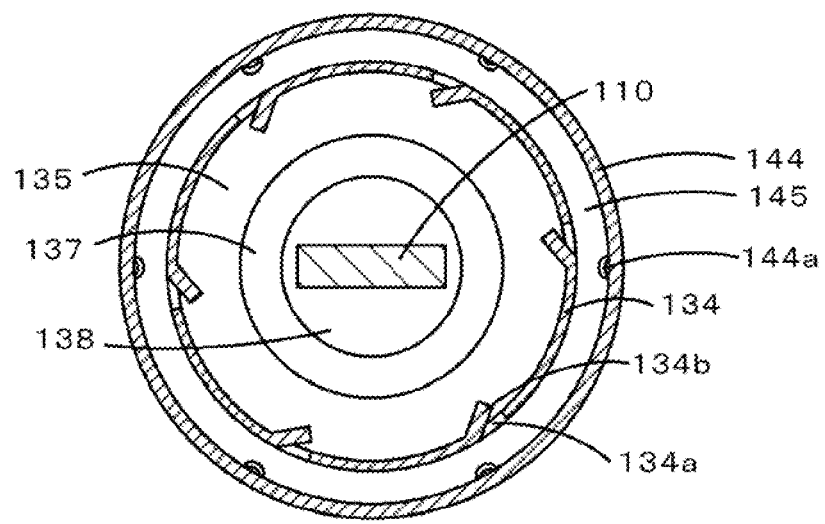
FIG. 3 is an A-A sectional view of FIG. 2.

One embodiment of practicing the present invention is described below with reference to the accompanied drawings. FIG. 1 is an explanatory view of a gas concentration detection sensor 100 attached to piping 200. FIG. 2 is a vertical sectional view of the structure of the gas concentration detection sensor 100. FIG. 3 is an A-A sectional view of FIG. 2.

As shown in FIG. 1, the gas concentration detection sensor 100 is located inside the piping 200 formed as an exhaust path from a vehicle engine and is designed to detect the concentration of at least one gas component among various gas components, such as NOx and O, included in omission or exhaust gas from the engine as an object gas to be measured.

As shown in FIG. 2, the gas concentration detection sensor 100 has a sensor element 110 having a function of measuring the concentration of a selected gas component included in the object gas to be measured, and a protective cover 120 protecting the sensor element 110.

The sensor element 110 is constructed as a long plate element having an oxygen ion conductive solid electrolyte layer of, for example, zirconia ($ZrO_2$). The sensor element including a base end 110b extending inside of metal main clamp 102 and a free end 110a that is covered by protective cover 120. The sensor element 110 includes a built-in heater having a temperature control function of heating the sensor element 110 and keeping the sensor element 110 warm. This structure of the sensor element 110 and the principle of measuring the concentration of a gas component are known in the art and are described in, for example, Patent Document JP 2008-164411A.

The protective cover 120 is arranged to surround the periphery of the sensor element 110. The protective cover 120 includes an inner protection cover 130 covering over an edge of the sensor element 110, and an outer protection cover 140 covering over the inner protection cover 130. A first gas chamber 122 and a second gas chamber 126 are formed as spaces defined by the inner protection cover 130 and the outer protection cover 140. A sensor element chamber 124 is formed as a space defined by the inner protection cover 130.

The inner protection cover 130 is a metal (for example, stainless steel) member having a cylindrical large-diameter section 132, a first cylindrical stem section 134 having a smaller diameter than the diameter of the large-diameter section 132, a second cylindrical stem section 136 having a smaller diameter than the diameter of the first stem section 134, and a bottomed cylindrical edge section 138 having a smaller diameter than the diameter of the second stem section 136. The inner protection cover 130 also has a step element 133 connecting the large-diameter section 132 with the first stem section 134, a step element 135 connecting the first stem section 134 with the second stem section 136, and a step element 137 connecting the second stem section 136 with the edge section 138. The large-diameter section 132, the first stem section 134, the second stem section 136, and the edge section 138 have an identical central axis. The large-diameter section 132 has an inner circumference that is in contact with a metal main clamp 102 of sensor element 110, such that the inner protection cover 130 is fastened to the main clamp 102. The first stem section 134 and the second stem section 136 are located to cover over a side face of the sensor element 110 and edge section 138 is located to cover free end 110a of sensor element 110, as shown in FIG. 2. Six inner gas apertures 134a (FIG. 3) are formed to communicate with the first gas chamber 122 and with the sensor element chamber 124 and six guide plates 134b provided to control the respective flows of the object gas running through the respective inner gas apertures 134a into the sensor element chamber 124 are arranged respectively at equal intervals around the first stem section 134 (see FIG. 3). The inner gas apertures 134a and the guide plates 134b are arranged in one-to-one corresponding relation. Each of the guide plates 134b is located between corresponding one of the inner gas apertures 134a and the sensor element 110. The multiple guide plates 134b are arranged to be rotationally symmetric (6-fold symmetry). Six gas passing apertures 138a are formed to communicate with the sensor element chamber 124 and with the second gas chamber 126 and are arranged at equal intervals around a side face of the edge section 138. The gas passing apertures 138a each has a circular cross section perpendicular to the central axis of the gas passing aperture 138a.

Figure 4:
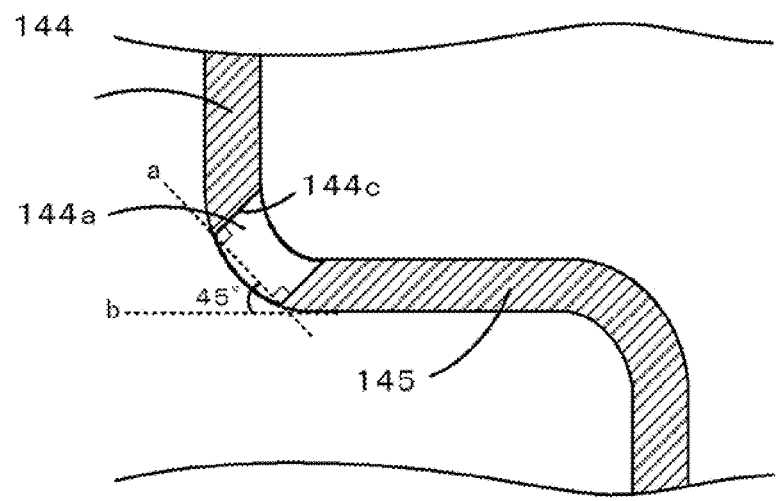
Figure 5:
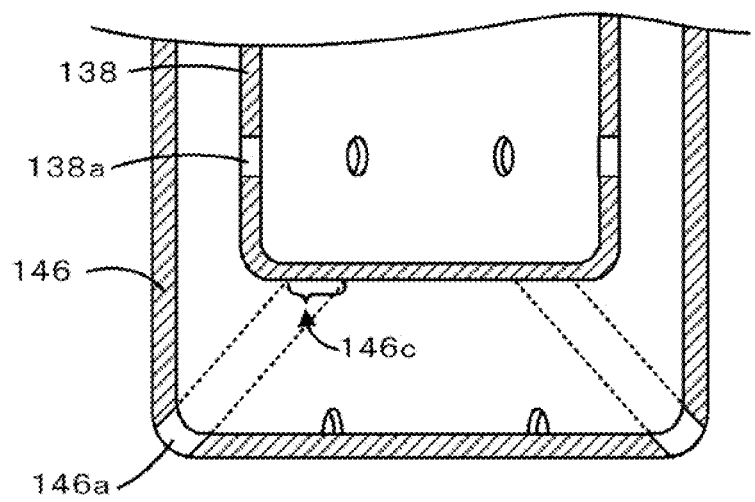

The outer protection cover 140 is a metal (for example, stainless steel) member having a cylindrical large-diameter section 142, a cylindrical stem section 144 connecting to the large-diameter section 142 and having a smaller diameter than the diameter of the large-diameter section 142, and a bottomed cylindrical edge section 146 having a smaller diameter than the diameter of the stem section 144. The outer protection cover 140 further has a step element 145 connecting the stem section 144 with the edge section 146. The large-diameter section 142, the stem section 144, and the edge section 146 each have a central axis identical to that of the inner protection cover 130. The large-diameter section 142 has an inner circumferential face that is in contact with the main clamp 102 and with the large-diameter section 132, such that the outer protection cover 140 is fastened to the main clamp 102. The stem section 144 is located to cover over an outer circumferential face of the first stem section 134 and that of the second stem section 136. Six first outer gas apertures 144a formed to communicate with the outside of the outer protection cover 140 and with the first gas chamber 122 are arranged at equal intervals around the stem section 144. The first outer gas apertures 144a are circular holes located in a first corner 144b, serving as a boundary portion between a side face of the stem section 144 and a bottom face of the step element 145. The first outer gas apertures 144a are formed such that the outer opening plane of each first outer gas aperture 144a forms an angle of 45 degrees with the bottom face of the step element 145 and the outer opening plane forms an angle of 90 degrees with an inner circumferential face of the first outer gas aperture 144a. Although the first outer gas apertures 144a are formed such that the outer opening plane forms an angle of 90 degrees with the inner circumferential face, the embodiment is not especially limited to the arrangement. For example, when an angle of 90 degrees or more is formed, advantages of the present invention are achieved. FIG. 4 is an enlarged partial sectional view of a portion including the first outer gas aperture 144a in FIG. 2. As shown in FIG. 4, the outer opening plane (broken line a) of the first outer gas aperture 144a forms an angle of 45 degrees with the bottom face (broken line b) of the step element 145. The inner circumferential face 144c of the first outer gas aperture 144a forms an angle of 90 degrees with the outer opening plane (broken line a) thereof. The edge section 146 is located to cover over the edge section 138 and an inner circumferential face of the edge section 146 is in contact with an outer circumferential face of the second stem section 136, as shown in FIG. 2. Six second outer gas apertures 146a formed to communicate with the outside of the outer protection cover 140 and with the second gas chamber 126 are arranged at equal intervals in a second corner 146b, serving as a boundary portion between a side face and a bottom face of the edge section 146. The second corner 146b is a boundary portion between a side face 140a and a bottom face 140b of outer protection cover 140. The second outer gas apertures 146a are circular holes formed in a manner similar to the first outer gas apertures 144a such that the outer opening plane of each second outer gas aperture 146a forms an angle of 45 degrees with the bottom face of the edge section 146 and the outer opening plane forms an angle of 90 degrees with an inner circumferential face of the second outer gas aperture 146a, as shown in FIG. 5. The positional relationship between each of the second outer gas apertures 146a and corresponding one of the gas passing apertures 138a is defined such that the gas passing aperture 138a is located at a position other than the region on the extension of the second outer gas aperture 146a, as described below. FIG. 5 is an enlarged partial sectional view of a portion including the second outer gas apertures 146a and the gas passing apertures 138a in FIG. 2. As shown in FIG. 5, when light having directivity is virtually applied from a direction along the central axis of each second outer gas aperture 146a (a direction which forms an angle of 45 degrees with the direction along the central axis of the outer protection cover 140), a region 146c irradiated with the light appears on a bottom face of the edge section 138 of the inner protection cover 130. This region 146c is referred to as the region on the extension of the second outer gas aperture 146a. The gas passing aperture 138a is located in a position other than the region 146c. The six first outer gas apertures 144a have the same area of opening and the six second outer gas apertures 146a have the same area of opening. The opening area of each second outer gas aperture 146a is larger than that of the first outer gas aperture. Since the first outer gas apertures 144a are equal in number (six) to the second outer gas apertures 146a, therefore, the total area (the area of each aperture x the number of apertures) of the second outer gas apertures 146a is larger than that of the first outer gas apertures 144a. The first outer gas apertures 144a each has a circular cross section perpendicular to the central axis of the first outer gas aperture 144a, and the second outer gas apertures 146a each has a circular cross section perpendicular to the central axis of the second outer gas aperture 146a. The first outer gas apertures 144a and the second outer gas apertures 146a may have a diameter that is not specifically restricted; for example, the first outer gas apertures 144a have a diameter in a range of 0.8 to 1.2 mm and the second outer gas apertures 146a have a diameter in a range of 0.8 to 1.2 mm in the present embodiment.

The first gas chamber 122 is a space defined by the step elements 133 and 135, the first stem section 134, the second stem section 136, the large-diameter section 142, the stem section 144, and the step element 145 as shown in FIG. 2. The sensor element chamber 124 is a space defined by the inner protection cover 130. The second gas chamber 126 is a space defined by the step element 137 and the edge sections 138 and 146. Since the inner circumferential face of the edge section 146 is in contact with the outer circumferential face of the second stem section 136, the first gas chamber 122 does not directly communicate with the second gas chamber 126.

The flow of the object gas in detection of the concentration of the gas component by the gas concentration detection sensor 100 having the structure explained above is described below. The flow of the object gas in a transient state caused, for example, when the flow rate of the object gas running in the piping 200 sharply increases is first described. In this state, the object gas running in the piping 200 flows through the first outer gas apertures 144a and the second outer gas apertures 146a into the outer protection cover 140. Since the total opening area of the second outer gas apertures 146a is larger than that of the first outer gas apertures 144a, the amount of object gas flowing through the second outer gas apertures 146a is larger than that through the first as apertures 144a. This causes a pressure acting from the second gas chamber 126 through the gas passing apertures 138a into the sensor element chamber 124 and further acting from the sensor element chamber 124 through the inner gas apertures 134a into the first gas chamber 122 in the transient state. This pressure pushes water in the first gas chamber 122 out of the outer protection cover 140 through the first outer gas apertures 144a, thus lowering the probability that water reaches the sensor element chamber 124 via the first gas chamber 122. Since each of the gas passing apertures 138a is disposed in a position other than the extension of the corresponding one of the second outer gas apertures 146a, this arrangement prevents water entering through the second outer gas apertures 146a in the transient state from reaching the sensor element chamber 124. Such arrangements prevent water from adhering to the sensor element 110.

The flow of the object gas in a state other than the transient state is described below. In this state, since the edge section 146 of the outer protection cover 140 is bottomed cylindrical, the flow of the object gas along the bottom face of the edge section 146 removes the object gas in the second gas chamber 126 such that the gas is sucked out through the second outer gas apertures 146a. In a state other than the transient state, therefore, the object gas enters the first gas chamber 122 through the first outer gas apertures 144a, passes from the first gas chamber 122 through the sensor element chamber 124 and the second gas chamber 126, and flows out through the second outer gas apertures 146a. Since the total area of the second outer gas apertures 146a is larger than that of the first outer gas apertures 144a, a force to suck out the object gas through the second outer gas apertures 146a is large. The first outer gas apertures 144a are arranged in the first corner 144b and the outer opening plane of each first outer gas aperture 144a forms an angle of 45 degrees with the bottom face of the step element 145. In this arrangement, the first outer gas apertures 144a allow the object gas, entering the first gas chamber 122 through the first outer gas apertures 144a, to flow toward a base end 110b of the sensor element 110 (upward in FIG. 2). Such arrangements reduce the time to replace a gas in the protective cover 120 with the object gas, compared with a structure in which the first outer gas apertures 144a are arranged around a side face of the outer protection cover 140. In other words, the response of the gas concentration detection sensor 100 is enhanced.

The first outer gas apertures 144a are arranged in the first corner 144b and the outer opening plane of each first outer gas aperture 144a forms an angle of 45 degrees with the bottom face of the step element 145. The second outer gas apertures 146a are arranged in the second corner 146b, the outer opening plane of each second outer gas aperture 146a forms an angle of 45 degrees with the bottom face of the edge section 146, and the outer opening plane forms an angle of 90 degrees with an inner circumferential face of the second outer gas aperture 146a. This arrangement facilitates the discharge of water entering the outer protection cover 140 to the outside through the second outer gas apertures 146a, compared with a structure in which the first outer gas apertures 144a and the second outer gas apertures 146a are arranged around the side face of the outer protection cover 140. This arrangement also prevents water from entering the sensor element chamber 124 and adhering to the sensor element 110.

The six first outer gas apertures 144a are arranged at equal intervals and the six second cuter gas apertures 146a are arranged at equal intervals. If the object gas flows from any direction on an outer circumferential face of the outer protection cover 140, therefore, at least one first outer gas aperture 144a and at least one second outer gas aperture 146a facing the upstream side of the object gas are surely present and at least one first outer gas apertures 144a and at least one second outer gas apertures 146a facing the downstream side of the object gas are surely present. This arrangement ensures that the object gas is introduced into the outer protection cover 140 and the inner protection cover 130 and the sensor element 110 detects the concentration of a gas component, irrespective of the orientation of the gas concentration detection sensor 100 located inside the piping 200.

In the structure of the embodiment described in detail above, the first outer gas apertures 144a and the second outer gas apertures 146a are arranged in the above-described positions so as to form the above-described angles. This structure prevents water from adhering to the sensor element 110. The first outer gas apertures 144a are arranged in the above-described portion so as to form the above-described angle, thus enhancing the response of the gas concentration detection sensor 100. The total opening area of the second outer gas apertures 146a is larger than that of the first outer gas apertures 144a, thus more effectively preventing water from adhering to the sensor element 110 and further enhancing the response of the gas concentration detection sensor 100. The six first outer gas apertures 144a are arranged at equal intervals and the six second outer gas apertures 146a are arranged at equal intervals. This arrangement ensures that the object gas is introduced into the outer protection cover 140 and the inner protection cover 130 and the sensor element 110 detects the concentration of a gas component.

The invention is not limited to the embodiment discussed above but may be actualized in diversity of other embodiments and applications within the scope of the invention.

The six first outer gas apertures 144a and the six second outer gas apertures 146a are arranged in the embodiment discussed above. This arrangement is, however, not restrictive, but the first outer gas apertures 144a may be three or more apertures arranged at equal intervals and the second outer gas apertures 146a may be three or more apertures arranged at equal intervals. In such an arrangement, at least one first outer gas aperture 144a and at least one second outer gas aperture 146a facing the upstream side of the object gas are surely present and at least one first outer gas aperture 144a and at least one second outer gas aperture 146a facing the downstream side of the object gas are surely present in a manner similar to the above-described embodiment, so that the object gas can be surely introduced into the outer protection cover 140 and the inner protection cover 130. Two first outer gas apertures 144a and two second outer gas apertures 146a may be arranged in outer protective cover 130. In this arrangement, so long as the gas concentration detection sensor 100 is located inside the piping 200 such that one first outer gas aperture 144a and one second outer gas aperture 146a facing the upstream side of the object gas are present and the other first outer gas aperture 144a and the other second outer gas aperture 146a facing the downstream side of the object gas are present, the object gas can be surely introduced into the outer protection cover 140 and the inner protection cover 130. It is not necessary to arrange the first outer gas apertures 144a and the second outer gas apertures 146a respectively at equal intervals.

In the embodiment discussed above, the six first outer gas apertures 144a have the same area of opening and the six second outer gas apertures 146a have the same area of opening. The arrangement is, however, not restrictive, but the gas apertures may have different areas of opening. In such an arrangement, so long as the total area of openings of the second outer gas apertures 146a is larger than that of the first outer gas apertures 144a, a pressure sufficient to push water in the first gas chamber 122 out of the outer protection cover 140 through the first outer gas apertures 144a in the transient state and a force strong enough to suck out the object gas through the second outer gas apertures 146a in a state other than the transient state are obtained. If the total area of openings of the second outer gas apertures 146a is equal to or less than that of the first outer gas apertures 144a, the arrangement of the first outer gas apertures 144a in the first corner 144b and the arrangement of the second outer gas apertures in the second corner 146b prevent water from adhering to the sensor element 110 and enhance the response of the gas concentration detection sensor 100.

Figure 6:
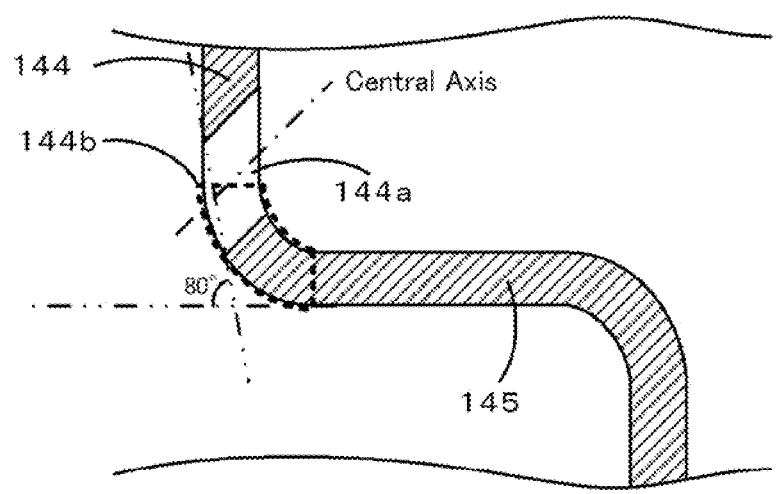
FIG. 6 is an enlarged partial sectional view of a portion including a first outer gas aperture 144a with a formed angle changed.
Figure 6:
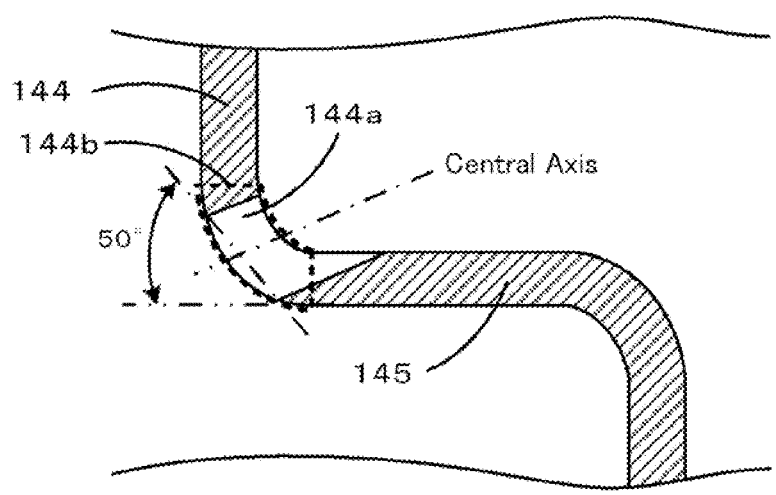

In the embodiment discussed above, the outer opening plane of each first outer gas aperture 144a forms an angle of 45 degrees with the bottom face of the step element 145. This arrangement is, however, not restrictive. For example, the formed angle may be in a range of 10 degrees to 80 degrees. In such an arrangement, so long as the first outer gas apertures 144a are arranged in the first corner 144b, the discharge of water to the outside through the first outer gas apertures 144a is facilitated and adhesion of water to the sensor element 110 is prevented. The phrase "the first outer gas apertures 144a are arranged in the first corner 144b" means that the first outer gas aperture 144a includes or overlaps with at least part of the first corner 144b which is a boundary portion between the side face of the stem section 144 and the step element 145. In the case where the formed angle is other than 45 degrees, as shown in FIG. 6(a), the first outer gas aperture may be formed at a different (shifted) position while an angle of the central axis of the first outer gas aperture 144a (that is, an angle of piercing the first outer gas aperture 144a) is 45 degrees similarly to the first gas aperture depicted in FIG. 2. In the case where the formed angle is other than 45 degrees, otherwise, as shown in FIG. 6(b), the first outer gas aperture 144a may be formed to have a different angle of the central axis from the first gas aperture depicted in FIG. 2. In FIG. 6(a) and FIG. 6(b), the portion defined by the dotted line is the first corner 144b, and the dashed-dotted line is the central axis of the first outer gas aperture 144a. In FIG. 6(a) and FIG. 6(b), the outer opening plane of each first outer gas aperture 144a forms an angle of 80 degrees and an angle of 50 degrees respectively with the bottom face of the step element 145. The first outer gas apertures 144a depicted in FIG. 6(a) and FIG. 6(b) include at least part of the corner 144b, and the outer opening plane of each first outer gas aperture 144a forms an angle in a range of 10 degrees to 80 degrees with the bottom face of the step element 145. Such an arrangement prevents water from adhering to the sensor element 110. Similarly to the first outer gas aperture 144a, although the outer opening plane of each second outer gas aperture 146a forms an angle of 45 degrees with the bottom face of the edge section 146 in the embodiment described above, the formed angle may be in the range of 10 degrees to 80 degrees. In such an arrangement, so long as the second outer gas apertures 146a are arranged in the second corner 146b, the discharge of water to the outside through the second outer gas apertures 146a is facilitated and adhesion of water to the sensor element 110 is prevented. The phrase "the second outer gas apertures 146a are arranged in the second corner 146b" means that the second outer gas aperture 146a includes or overlaps with at least part of the second corner 146b which is a boundary portion between the side face and the bottom face of the edge section 146. Second corner 146b also is a boundary portion between side face 140a and bottom face 140b of outer protection cover 140.

Figure 7:
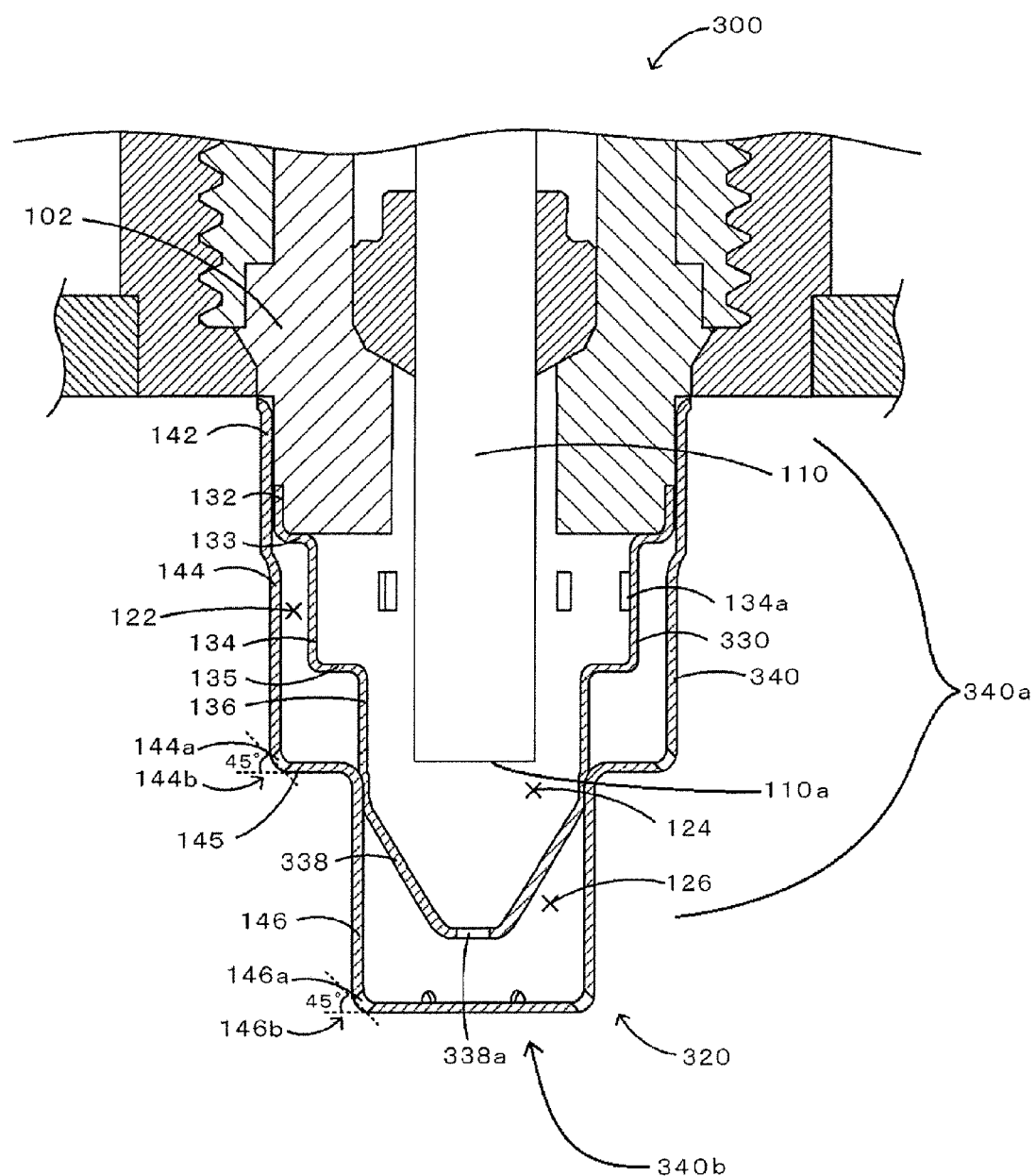
FIG. 7 is a vertical sectional view of the structure of a gas concentration detection sensor 300 in one modified structure.

A gas concentration detection sensor 300 shown in FIG. 7 may be used instead of the gas concentration detection sensor 100 according to the above-described embodiment. The gas concentration detection sensor 300 includes, as a protective cover 320, an inner protection cover 330 and an outer protection cover 340. The inner protection cover 330 has a structure similar to that of the inner protection cover 130 in FIG. 2 with the exception that the shape of an edge section 338 differs from that of the edge section 138 and the shape of an gas passing aperture 338a differs from that of each gas passing aperture 138a and with the exception of excluding the step element 137. The components except the edge section 338 and the gas passing aperture 338a are therefore designated by the same reference numerals without duplicated explanation. Unlike the edge section 138, the edge section 338 is shaped in an inverted triangular frustum. The gas passing aperture 338a is a circular hole located at the central point of a bottom face of the edge section 338. Since the outer protection cover 340 has the same structure as that of the outer protection cover 140 in FIG. 2, the same reference numeral is assigned to the same component as that in FIG. 2 without duplicated explanation. The gas concentration detection sensor 300 having such a structure offers the same advantages as those of the embodiment discussed above.

Figure 8:
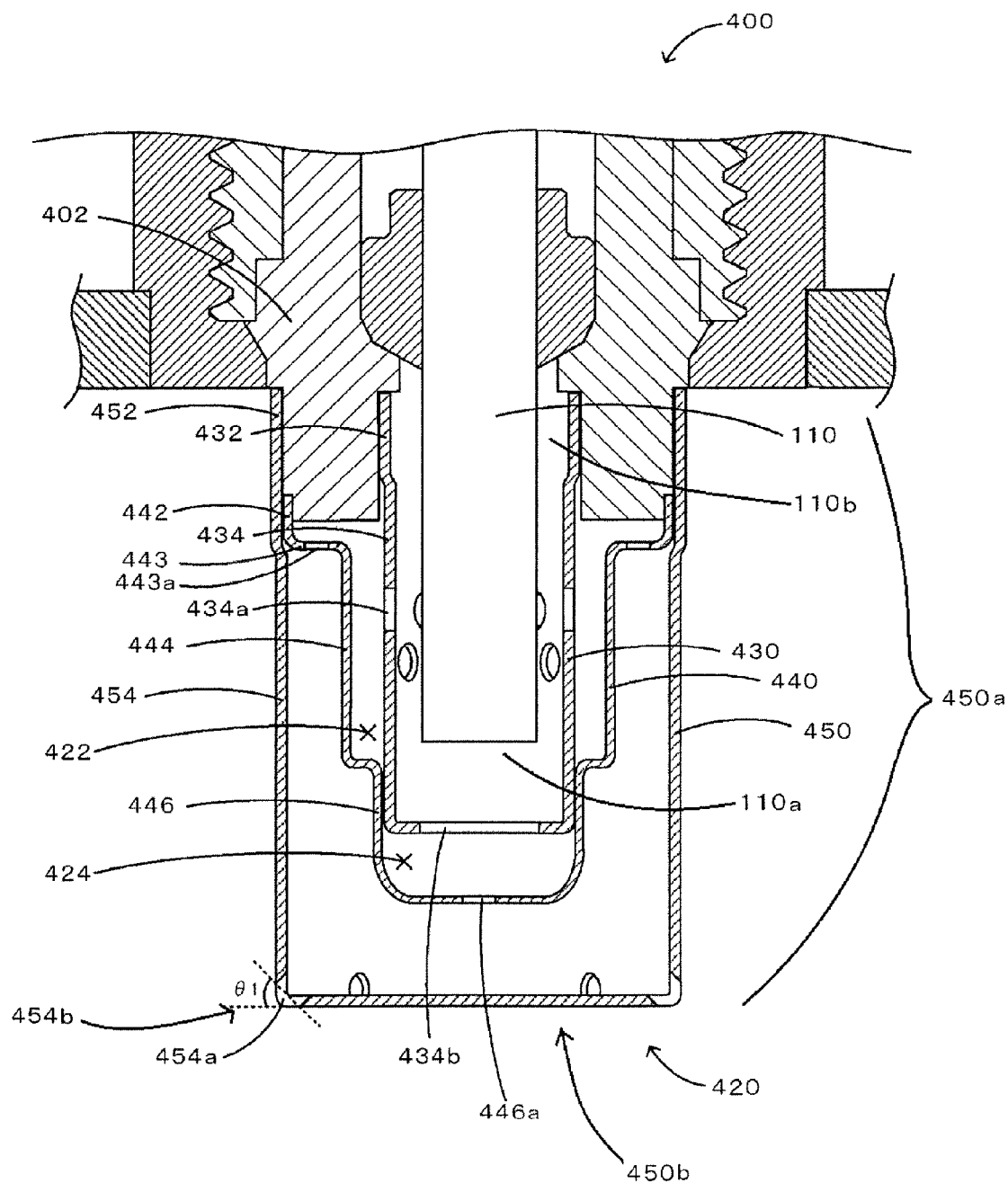
FIG. 8 is a vertical sectional view of the structure of a gas concentration detection sensor 400 in another modified structure.

A gas concentration detection sensor 400 shown in FIG. 8 may be used instead of the gas concentration detection sensor 100 according to the above-described embodiment. The gas concentration detection sensor 400 includes a protective cover 420 having a triple-layered structure, namely, including a first inner protection cover 430 covering over the free end 110a of the sensor element 110, a second inner protection cover 440 covering over the first inner protection cover 430, and an outer protection cover 450 covering over the second inner protection cover 440. The first inner protection cover 430 has an outer circumferential face that is in contact with a metal main clamp 402 and includes a cylindrical large-diameter section 432 and a bottomed cylindrical edge section 434. Twelve gas passing apertures 434a are arranged around a side face of the edge section 434. A gas passing aperture 434b is disposed at the center of a bottom face of the edge section 434. The gas passing apertures 434a are arranged at equal intervals such that they are axially (vertically in FIG. 8) staggered in two levels. The second inner protection cover 440 has an inner circumferential face that is in contact with the metal main clamp 402 and includes a cylindrical large-diameter section 442, a cylindrical stem section 444, and a bottomed cylindrical edge section 446. The large-diameter section 442 is connected to the stem section 444 through a step element 443. The stem section 444 is also connected to the edge section 446 through a step. Six inner gas apertures 443a are arranged at equal intervals on the step element 443. A gas passing aperture 446a is disposed at the center of a bottom face of the edge section 446. The outer protection cover 450 has an inner circumferential face that is in contact with the metal main clamp 402 and includes a cylindrical large-diameter section 452 and a bottomed cylindrical edge section 454. In a boundary portion between a side face and a bottom face of the edge section 454, six circular outer gas apertures 454a are arranged. The second corner 454b of edge section 454 is a boundary portion between side face 450a and bottom face 450b of outer protection cover 450. Each outer gas aperture 454a is formed such that an angle θ1 formed by the outer opening plane of the outer gas aperture 454a and the bottom face of the edge section 454 is in a range of 10 degrees to 80 degrees. The edge section 434 of the first inner protection cover 430 is in contact with the edge section 446 of the second inner protection cover 440, such that a space defined by the first inner protection cover 430 and the second inner protection cover 440 is divided into an upper chamber 422 and a lower chamber 424. The gas concentration detection sensor 400 having such a structure offers the following advantages. The structure facilitates the discharge of water entering the outer protection cover 450 to the outside through the outer gas apertures 454a, thus preventing water from entering the second inner protection cover 440 and the first inner protection cover 430 and adhering to the sensor element 110. The outer gas apertures 454a allow the object gas entering the outer protection cover 450 through the outer gas apertures 454a to flow toward the base end of the sensor element 110 (upward in FIG. 8). Since the inner gas apertures 443a are located closer to the base end 110b of the sensor element 110 than the outer gas apertures 454a as illustrated in the figure, the object gas entering through the outer gas apertures 454a tends to reach the inner gas apertures 443a. The structure reduces the time to replace a gas in the protection cover 420 with the object gas and thereby enhances the response of the gas concentration detection sensor.

Figure 9:
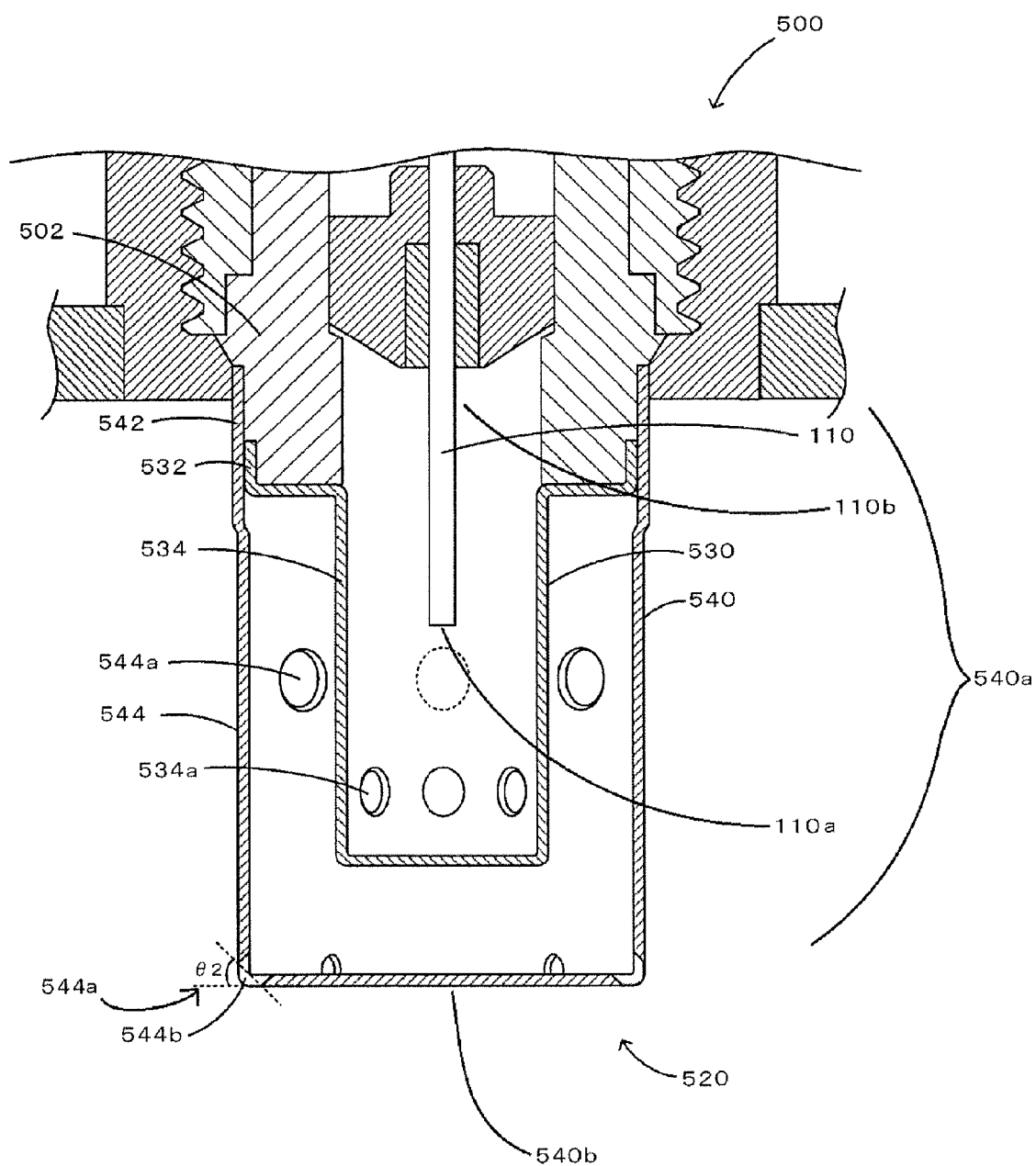
FIG. 9 a vertical sectional view of the structure of a gas concentration detection sensor 500 in another modified structure.

A gas concentration detection sensor 500 shown in FIG. 9 may be used instead of the gas concentration detection sensor 100 according to the above-described embodiment. The gas concentration detection sensor 500 includes a protective cover 520 having a double-layered structure, namely, including an inner protection cover 530 covering over the free end 110a of the sensor element 110 and an outer protection cover 540 covering over the inner protection cover 530. The inner protection cover 530 has an inner circumferential face that is in contact with a metal main clamp 502 and includes a cylindrical large-diameter section 532 and a bottomed cylindrical edge section 534. The large-diameter section 532 is connected to the edge section 534 through a step. Six inner gas apertures 534a are arranged at equal intervals around a side face of the edge section 534. The outer protection cover 540 has an inner circumferential face that is in contact with the metal main clamp 502 and includes a cylindrical large-diameter section 542 and a bottomed cylindrical edge section 544. Six gas passing apertures 544a are arranged at equal intervals around a side face of the edge section 544. The second corner 544a is a boundary portion between a side face 540a and a bottom face 540b of outer protection cover 540. Six circular outer gas apertures 544b are arranged in a boundary portion between the side face and a bottom face of the edge section 544. Each outer gas aperture 544b is formed such that an angle θ2 formed by the outer opening plane of the outer gas aperture 544b and the bottom face of the edge section 544 is in a range of 10 degrees to 80 degrees and the outer opening plane forms an angle of 90 degrees with an inner circumferential face of the outer gas aperture 544b. The gas concentration detection sensor 500 having such a structure also offers the following advantages. The structure facilitates the discharge of water entering the outer protection cover 540 to the outside through the outer gas apertures 544b, thus preventing water from entering the inner protection cover 530 and adhering to the sensor element 110. The outer gas apertures 544b allow the object gas entering the outer protection cover 540 through the outer gas apertures 544b to flow toward the base end of the sensor element 110 (upward in FIG. 9). Since the inner gas apertures 534a are located closer to the base end 110b of the sensor element 110 than the outer gas apertures 544b as illustrated in FIG. 9, the object gas entering through the outer gas apertures 544b tends to reach the inner gas apertures 534a. This structure reduces the time to replace a gas in the protection cover 520 with the object gas, thus enhancing the response of the gas concentration detection sensor.

Figure 10:
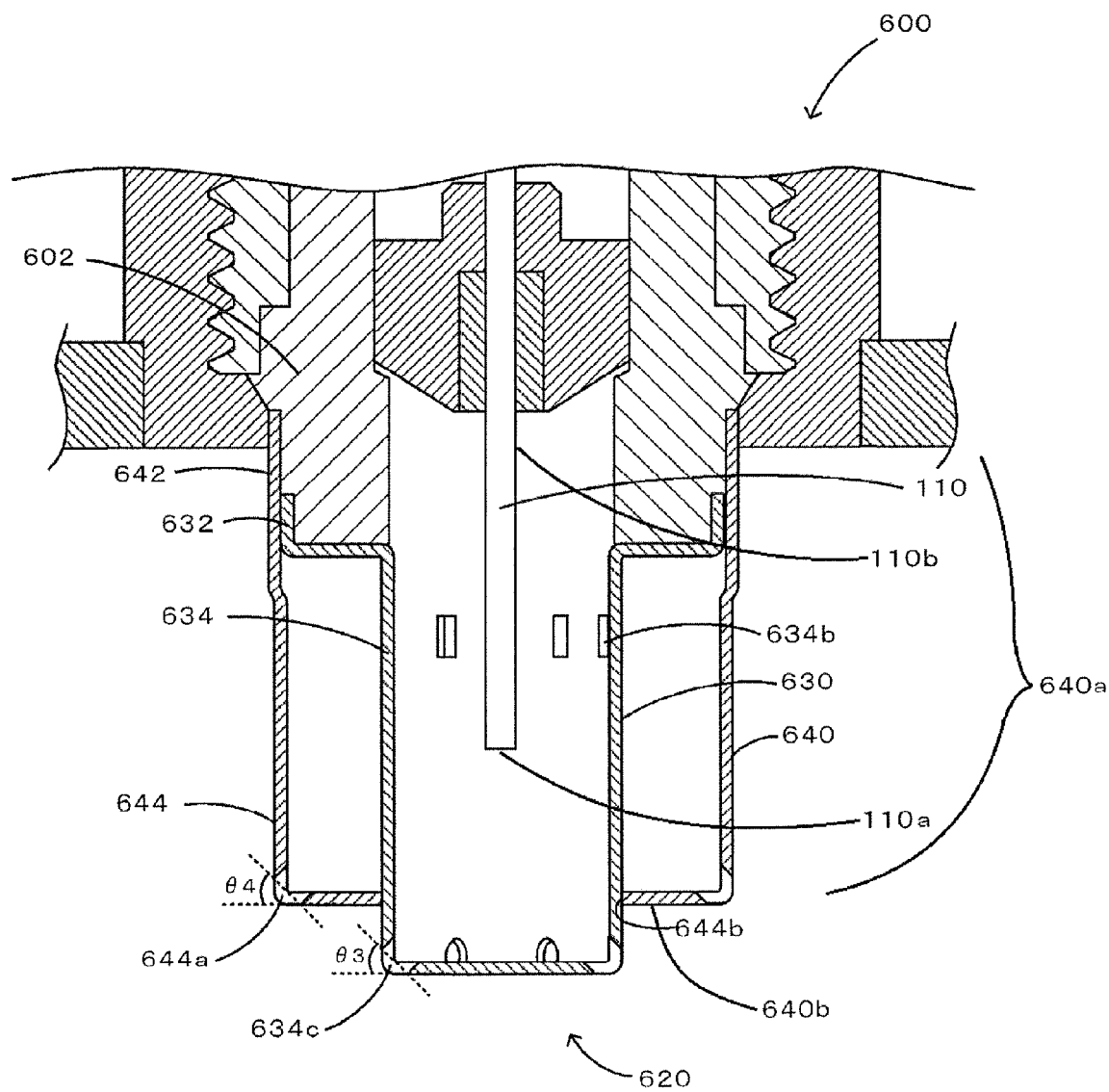
FIG. 10 a vertical sectional view of the structure of a gas concentration detection sensor 600 in another modified structure.

A gas concentration detection sensor 600 shown in FIG. 10 may be used instead of the gas concentration detection sensor 100 according to the above-described embodiment. The gas concentration detection sensor 600 includes a protective cover 620 having a double-layered structure, namely, including an inner protection cover 630 covering over the free end 110a of the sensor element 110 and an outer protection cover 640. The inner protection cover 630 has an inner circumferential face that is in contact with a metal main clamp 602 and includes a cylindrical large-diameter section 632 and a bottomed cylindrical edge section 634. The large-diameter section 632 is connected to the edge section 634 through a step. Six inner gas apertures (not shown) formed to allow the object gas to flow inside and outside the inner protection cover 630 are arranged at equal intervals and six guide plates 634b provided to control the respective flows of the object gas running through the respective inner gas apertures into the inner protection cover 630 are arranged at equal intervals around the edge section 634. The inner gas apertures and the guide plates 634b are the same as the inner gas apertures 134a and the guide plats 134b shown in FIGS. 2 and 3. Six circular gas passing apertures 634c are arranged in a boundary portion between a side face and a bottom face of the edge section 634. Each gas passing aperture 634c is formed such that an angle θ3 formed by the outer opening plane of the gas passing aperture 634c and the bottom face of the edge section 634 is in a range of 10 degrees to 80 degrees. The outer protection cover 640 has an inner circumferential face that is in contact with the metal main clamp 602 and includes a cylindrical large-diameter section 642 and an edge section 644 having a side face and a bottom face. The edge section 644 has an aperture on the bottom face, such that the edge section 634 of the inner protection cover 630 extends through this aperture. An inner circumferential face 644b of the aperture on the bottom face of the edge section 644 is welded to the side face of the edge section 634 of the inner protection cover 630. Six circular outer gas apertures 644a are arranged in a boundary portion between the side face and the bottom face of the edge section 644. The second corner 644b is a boundary portion between side face 640a and bottom face 640b of outer protection cover 640. Each outer gas aperture 644a is formed such that an angle θ4 formed by the outer opening plane of the outer gas aperture 644a and the bottom face of the edge section 644 is in a range of 10 degrees to 80 degrees. The gas concentration detection sensor 600 having such a structure also offers the following advantages. The structure facilitates the discharge of water entering the outer protection cover 640 and water entering the inner protection cover 630 to the outside through the outer gas apertures 644a and the gas passing apertures 634c, thus preventing the water from entering the inner protection cover 630 and adhering to the sensor element 110. The outer gas apertures 644a allow the object gas entering the outer protection cover 640 through the outer gas apertures 644a to flow toward the base end 110b of the sensor element 110 (upward in FIG. 10). As will be seen from the positional relationship between the guide plates 634b and the outer gas apertures 644a, the inner gas apertures are located closer to the base end of the sensor element 110 than the outer gas apertures 644a. The object gas entering through the outer gas apertures 644a therefore tends to reach the inner gas apertures. This structure reduces the time to replace a gas in the protection cover 620 with the object gas and thereby enhances the response of the gas concentration detection sensor.

Figure 11:
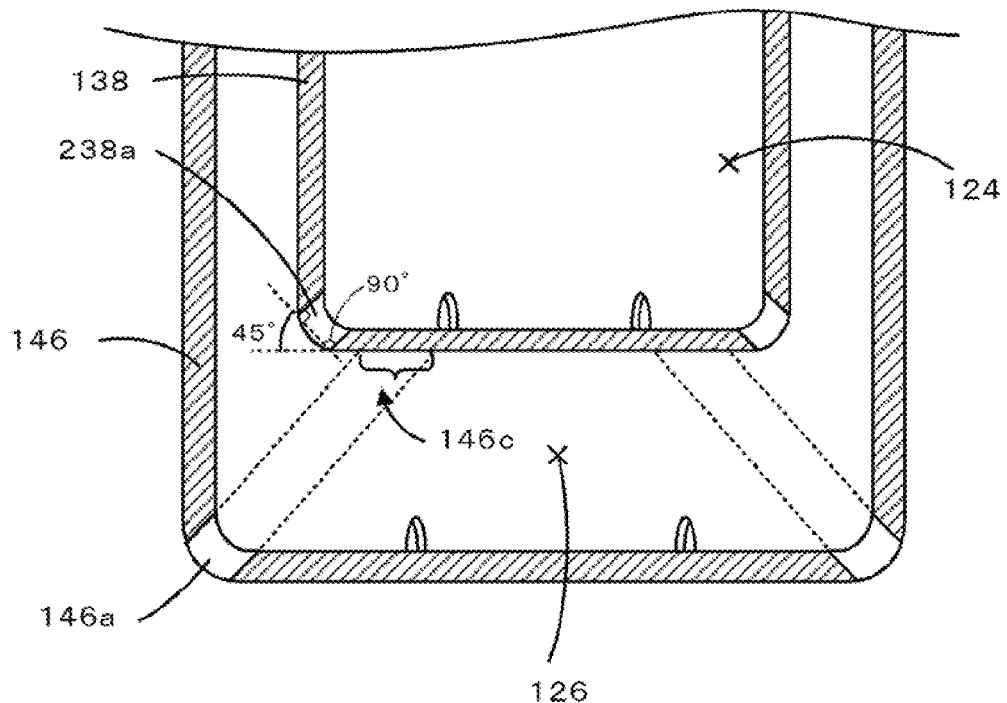
FIG. 11 is an enlarged partial sectional view of a portion including gas passing apertures 238a in one modified structure.

In the embodiment discussed above, the gas passing apertures 130a are located around the side face of the edge section 138 of the inner protection cover 130 as shown in FIGS. 2 and 5. The arrangement is, however, not restrictive, but the gas passing apertures 138a may be located in the boundary portion between the side face and the bottom face of the inner protection cover. FIG. 11 is an enlarged partial sectional view of a portion including the gas passing apertures in a modified structure in which the gas passing apertures are located in the boundary portion between the side face and the bottom face of the inner protection cover. In FIG. 11, the same reference numeral is assigned to the same component as that in FIG. 5 without duplicated explanation. As shown in the figure, unlike the gas passing apertures 138a in FIG. 5, gas passing apertures 238a in the modified structure are formed such that the outer opening plane of each gas passing aperture 238a forms an angle of 45 degrees with the bottom face of the edge section 138 of the inner protection cover 130 and the outer opening plane forms an angle of 90 degrees with the inner circumferential face of the gas passing aperture 238a. The angle formed by the outer opening plane of the gas passing aperture 238a and the bottom face of the edge section 138 of the inner protection cover 130 is not limited to 45 degrees but may be in a range of 10 degrees to 80 degrees. With this structure, the gas passing apertures 238a allow the object gas entering the second gas chamber 126 from the sensor element chamber 124 to flow toward the second outer gas apertures 146a. This structure facilitates the arrival of the object gas, entering the second gas chamber 126 from the sensor element chamber 124, at the second outer gas apertures 146a, compared with a structure in which the gas passing apertures are arranged on the side face or the bottom face of the edge section 138 and a structure in which the angle formed by the outer opening plane of each gas passing aperture and the bottom face of the edge section 138 is not in the range of 10 degrees to 80 degrees. This structure therefore reduces the time the object gas takes to reach the outside via the second gas chamber 126, thus enhancing the response of the gas concentration detection sensor. If the gas passing apertures 238a overlap the regions 146c, the advantages of enhancing the response of the gas concentration detection sensor are obtained.

Figure 12:
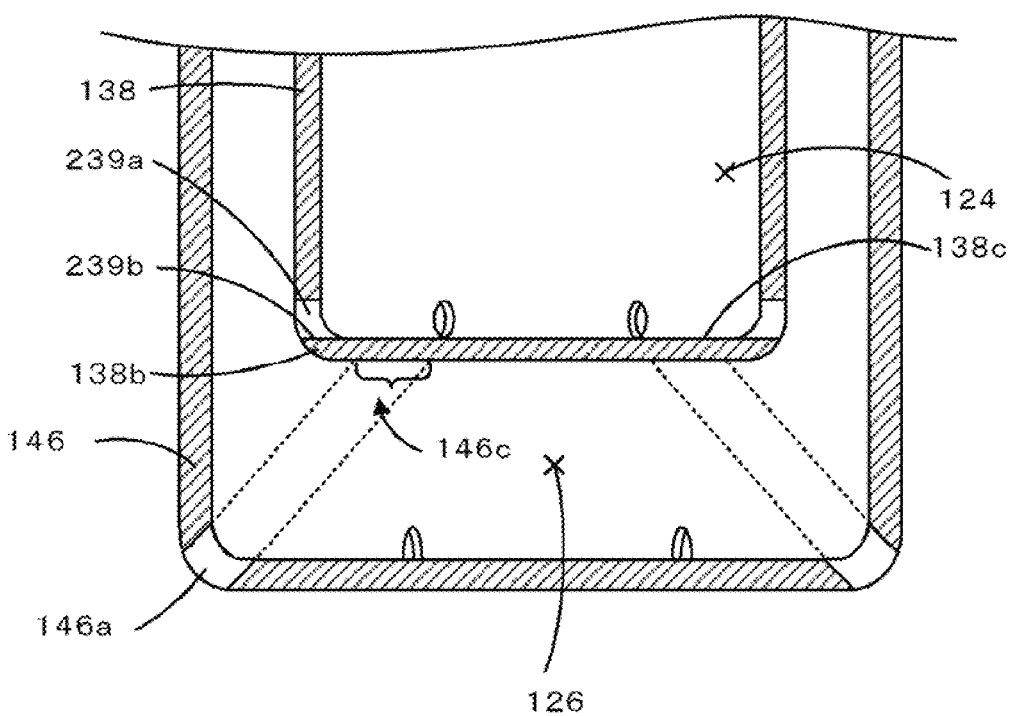
FIG. 12 is an enlarged partial sectional view of a portion including gas passing apertures 239a in another modified structure.

In the embodiment discussed above, the gas passing apertures 138a are located around the side face of the edge section 138 of the inner protection cover 130 as shown in FIGS. 2 and 5. The arrangement is, however, not restrictive, but the gas passing apertures 138a may be located at a position closer to the bottom face of the edge section 138 in the side face of the edge section 138, or at a position closer to the step element 137 in the side face of the edge section 138. FIG. 12 is an enlarged partial sectional view of a portion including gas passing apertures located around the side face and closer to the bottom face of the edge section 138. In FIG. 12, the same reference numeral is assigned to the same component as that in FIG. 5 without duplicated explanation. As shown in FIG. 12, the gas passing apertures 239a in this modified structure are located at a position closest, in the side face of the edge section 138, to the corner 138b of the edge section 138. The gas passing aperture 239a has a lowermost inner circumferential face of 239b which is flush with the inner side of the bottom face 138c of the edge section 138.

Figure 13:
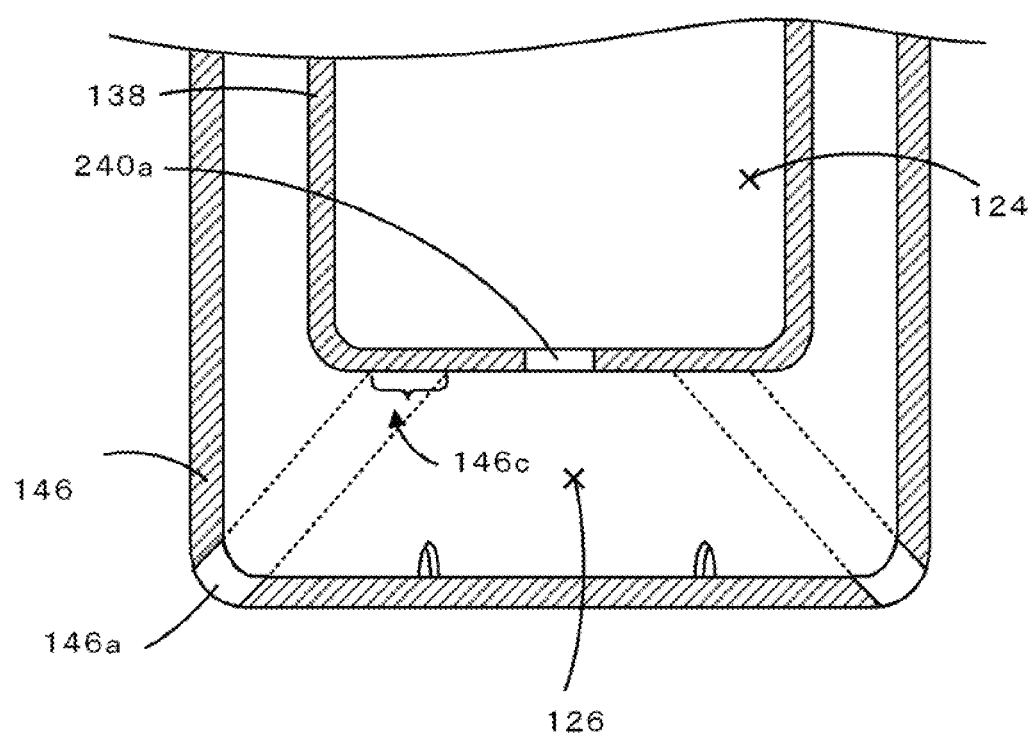
FIG. 13 is an enlarged partial sectional view of a portion including gas passing apertures 240a in another modified structure.
Figure 14:
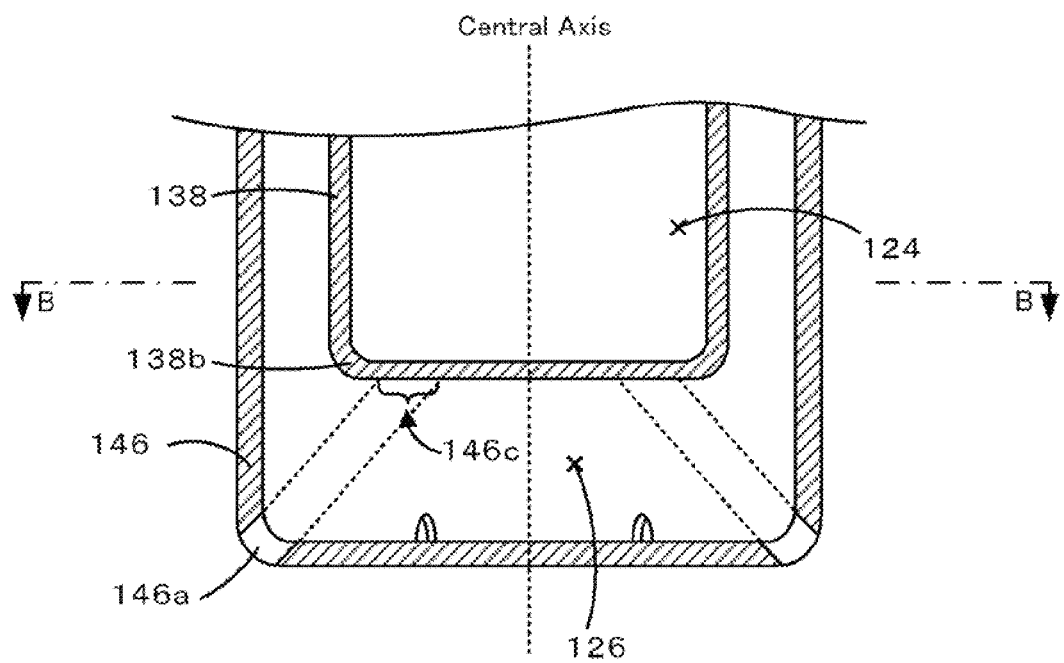
Figure 14:
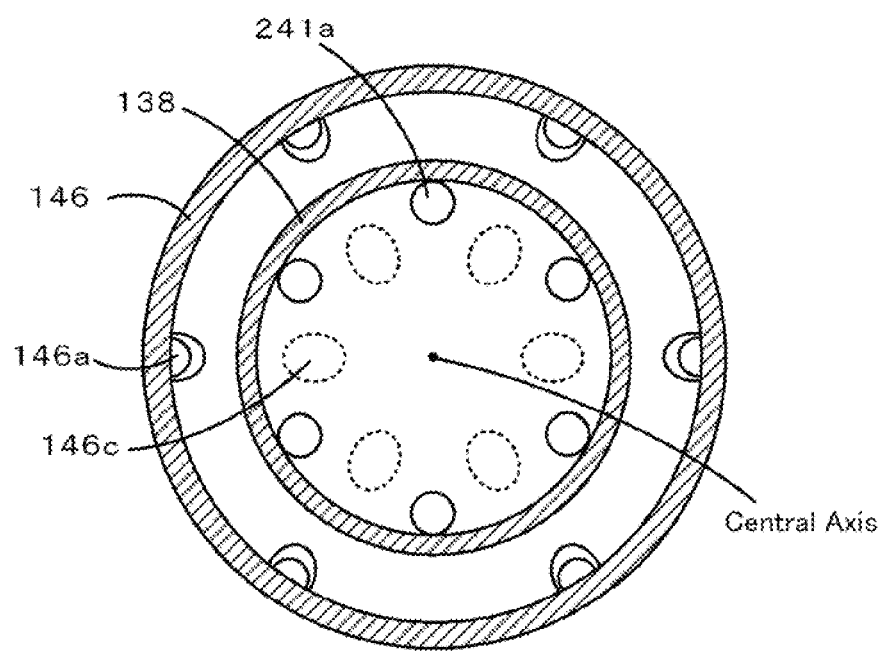

In the embodiment discussed above, the gas passing apertures 138a are located around the side face of the edge section 138 of the inner protection cover 130 as shown in FIGS. 2 and 5. The arrangement is, however, not restrictive, but the gas passing apertures 138a may be located in the bottom face of the edge section 138. FIG. 13 is an enlarged partial sectional view of a portion including gas passing apertures located in the bottom face of the edge section 138. In FIG. 13, the same reference numeral is assigned to the same component as that in FIG. 5 without duplicated explanation. As shown in FIG. 13, the gas passing aperture 240a in this modified structure is a circular aperture located at the center of the bottom face of the edge section 138. The gas passing aperture may be located at the position other than the center of the bottom face of the edge section 138. For example, the gas passing aperture may be located at the position, in the bottom race, closest to the corner portion of the edge section 138. The position of the gas passing aperture and the position of the region 146c as the region on the extension of the second outer gas aperture 146a may be phase-shifted with respect to the center point as the central axis of the edge section 138 when viewed in the direction along the central axis of the edge section 138 (vertically in FIG. 2), so that the gas passing aperture is located in a position other than the region 146c. This arrangement of positions the gas passing apertures is shown in FIG. 14. FIG. 14(a) is a partial sectional view of the edge section 138 and FIG. 14(b) is a B-B sectional view of FIG. 14(a). In FIG. 14, the same reference numeral is assigned to the same component as that in FIG. 5 without duplicated explanation. As shown in FIG. 14(b), six gas passing apertures 241a in this modified structure are arranged at equal intervals and located at the position, in the edge section 138, closest to the corner 138b. When viewed in the direction along the central axis as in FIG. 14(b), the gas passing apertures 241a are in contact with the inner circumferential face of the side face of the edge section 138. In addition, when viewed with respect to the central axis as the center point, the positions of the gas passing apertures 241a and the positions of the regions 146c are phase-shifted, and accordingly the gas passing apertures 241a do not overlap the regions 146c. In this arrangement, since the gas passing aperture 241a is located at a position other than the region 146e, the advantages of preventing water from entering in the sensor element chamber 121 can be obtained.

In the embodiment discussed above, the gas passing aperture 138a, the first outer gas aperture 144a, and the second outer gas aperture 146a each has a circular cross section perpendicular to its central axis. The arrangement is, however, not restrictive, but the cross section may be an ellipse or a polygon such as a rectangle.

EXAMPLES

Examples 1 and 2

A plurality of gas concentration detection sensors 100 shown in FIG. 2 were fabricated. Specifically, as regards the inner protection cover 130, the thickness was 0.3 mm, the axial length of the large-diameter section 132 was 1.9 mm, the axial length of the first stem section 134 was 5.2 mm, the axial length of the second stem section 136 was 5.2 mm, the axial length of the edge section 138 was 4.9 mm, the inner diameter of the large-diameter section 132 was 13.54 mm, the inner diameter of the first stem section 134 was 11.2 mm, the inner diameter of the second stem section 136 was 7.6 mm, the inner diameter of the edge section 138 was 5.3 mm, the length of the opening of each inner gas aperture was 1.5 mm, and the width thereof was 0.3 mm. As regards the outer protection cover 140, the thickness was 0.4 mm, the axial length of the large-diameter section 142 was 5.6 mm, the length of the stem section 144 was 9.2 mm, the axial length of the edge section 146 was 0.6 mm, the inner diameter of the large-diameter section 142 was 14.4 mm, the inner diameter of the stem section 144 was 13.8 mm, the inner diameter of the edge section 146 was 7.9 mm, and the bend radius R of each of the first corner 144b and the second corner 146b was 1.0 mm. The sensors were fabricated such that the inner diameter $\phi 1$ of the first outer gas aperture 144a of the outer protection cover 140 and the inner diameter $\phi 2$ of the second outer gas aperture 146a were variously changed as shown in Examples 1 and 2 in Table 1. The "angle of gas passing aperture" in Table 1 represents the angle formed by the outer opening plane of the gas passing aperture of the inner protection cover and the bottom face of the inner protection cover. In Examples 1 and 2, the angle of the gas passing apertures is 90 degrees. The sensor element 110 of each of the fabricated gas concentration detection sensors 100 was designed to detect the concentration of oxygen.

Examples 3 to 5

Gas concentration detection sensors having the same structure as Examples 1 and 2 were fabricated, except that the number of first outer gas apertures 144a, the number of second outer gas apertures 146a, the inner diameter $\phi 1$, and the inner diameter $\phi 2$ were set to values shown in Examples 3 to 5 in Table 1.

Examples 6 and 7, Comparative Examples 1 and 2

Figure 15:
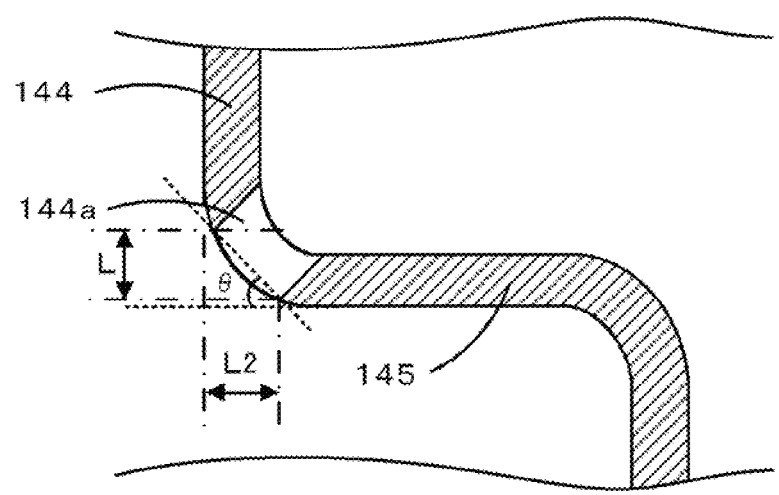
FIG. 15 is an explanatory view of the relationship between a formed angle θ and lengths L and L2.
Figure 16:
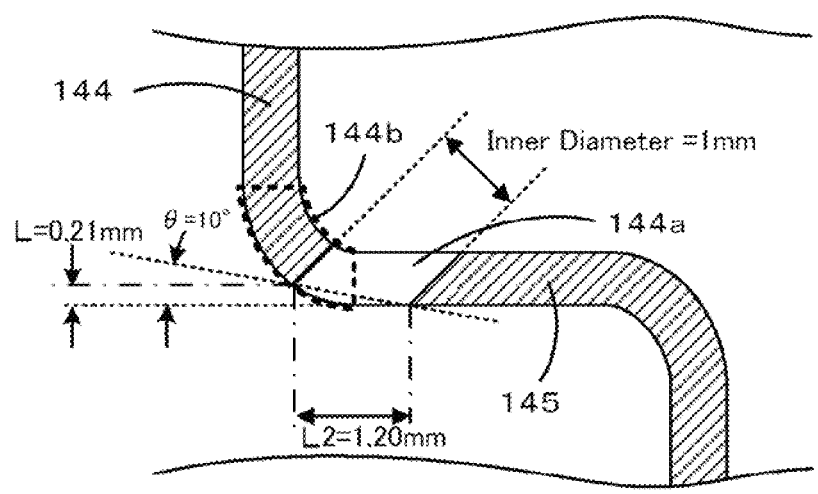
FIG. 16 is an explanatory view of the relationship between a formed angle θ and lengths L and L2 in Example 6 and Comparative Example 1.
Figure 16:
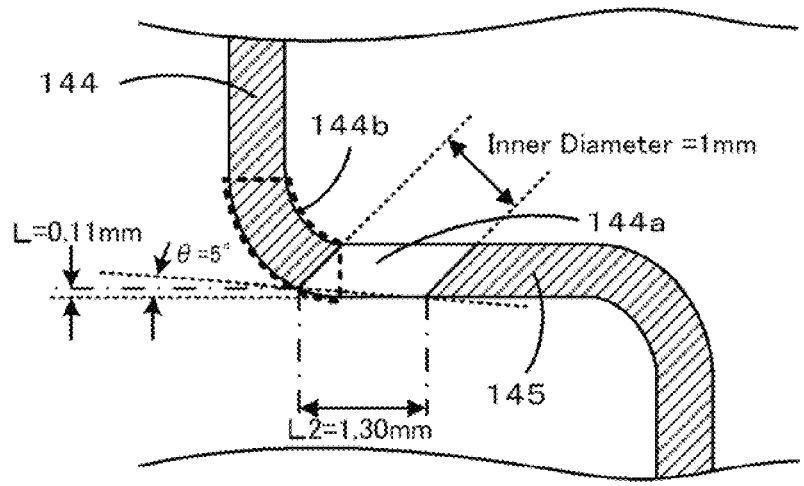
Figure 17:
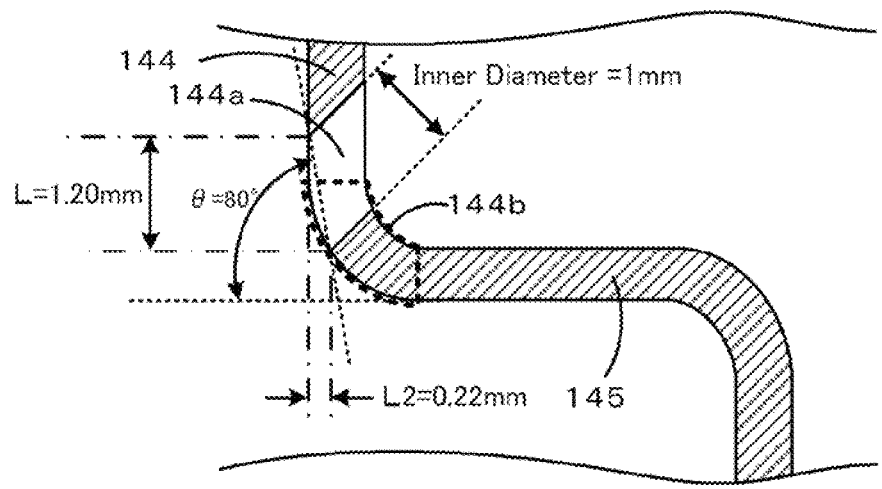
FIG. 17 is an explanatory view of the relationship between a formed angle θ and lengths L and L2 in Example 7 and Comparative Example 2.
Figure 17:
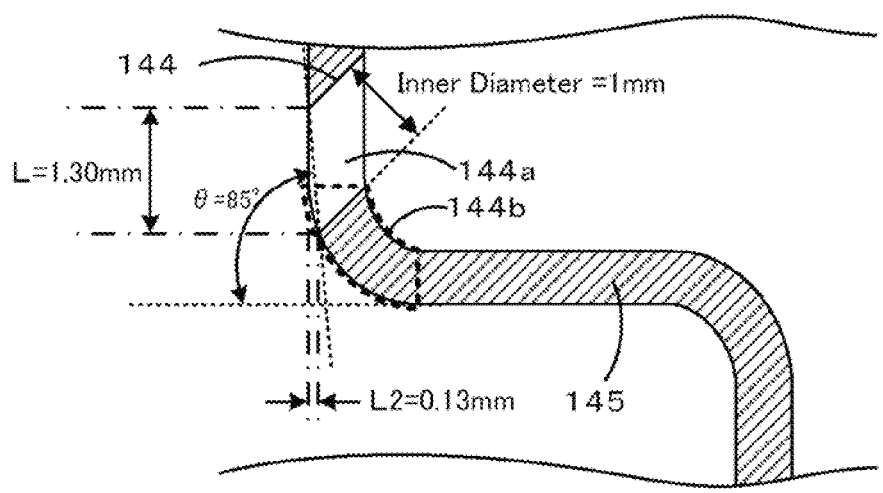

Gas concentration detection sensors having the same structure as Example 1 were fabricated as Examples 6 and 7 and Comparative Examples 1 and 2, except that the angle formed by the outer opening plane of each first outer gas aperture 144a and the bottom face of the step element 145 and the angle formed by the outer opening plane of each second outer gas aperture 146a and the bottom face of the edge section 146 were set to the same value θ and the value θ was changed as shown in Table 1. As shown in FIG. 6(a), the formed angle θ was changed by shifting the position of forming the apertures while the angle of the central axis of the first outer gas aperture 114a is 45 degrees similarly to the first gas aperture depicted in FIG. 2. Changing the formed angle θ changed the length L of the outer opening plane of each first outer gas aperture 144a along the central axis of the outer protection cover 140 and the length L2 the outer opening plane of each first outer gas aperture 144a from the outer circumferential face of the stem section 144 to the closest point to the central axis of the outer protection cover 140 (see, FIG. 15). The length L in Example 1 (the formed angle θ=45 degrees) was 0.71 mm. As the formed angle θ was decreased to 10 degrees and 5 degrees as in Example 6 and Comparative Example 1, the length L was decreased to 0.21 mm and 0.11 mm respectively and the lengths L2 was increased to 1.20 mm and 1.30 mm (see, FIG. 15). As the formed angle θ was increased to 80 degrees and 85 degrees as in Example 7 and Comparative Example 2, the length L was increased to 1.20 mm and 1.30 mm and the length L2 was decreased to 0.22 mm and 0.13 mm (FIG. 17). This relationship between the formed angle θ and the lengths L and L2 is the same as that in the second outer gas aperture 146a. As will be seen from FIGS. 16 and 17, in Examples 6 and 7 and Comparative Examples 1 and 2, the angle formed by the inner circumferential face of the first outer gas aperture 144a with the outer opening plane of the first outer gas aperture is not 90 degrees. The same applies to the second outer gas aperture 146a.

Example 8

A gas concentration detection sensor having the same structure as Example 2 was fabricated as Example 8, except that the edge section 138 of the inner protection cover 130 had the gas passing apertures 238a shown in FIG. 11 instead of the gas passing apertures 138a (specifically, the gas passing apertures 238a were located in the boundary portion between the side face and the bottom face of the edge section 138 and the outer opening plane of each gas passing aperture 238a formed an angle of 45 degrees with the bottom face of the edge section 138). Six gas passing apertures 238a each having an inner diameter of 1.0 mm were arranged at equal intervals.

Comparative Examples 3 to 5

Figure 18:
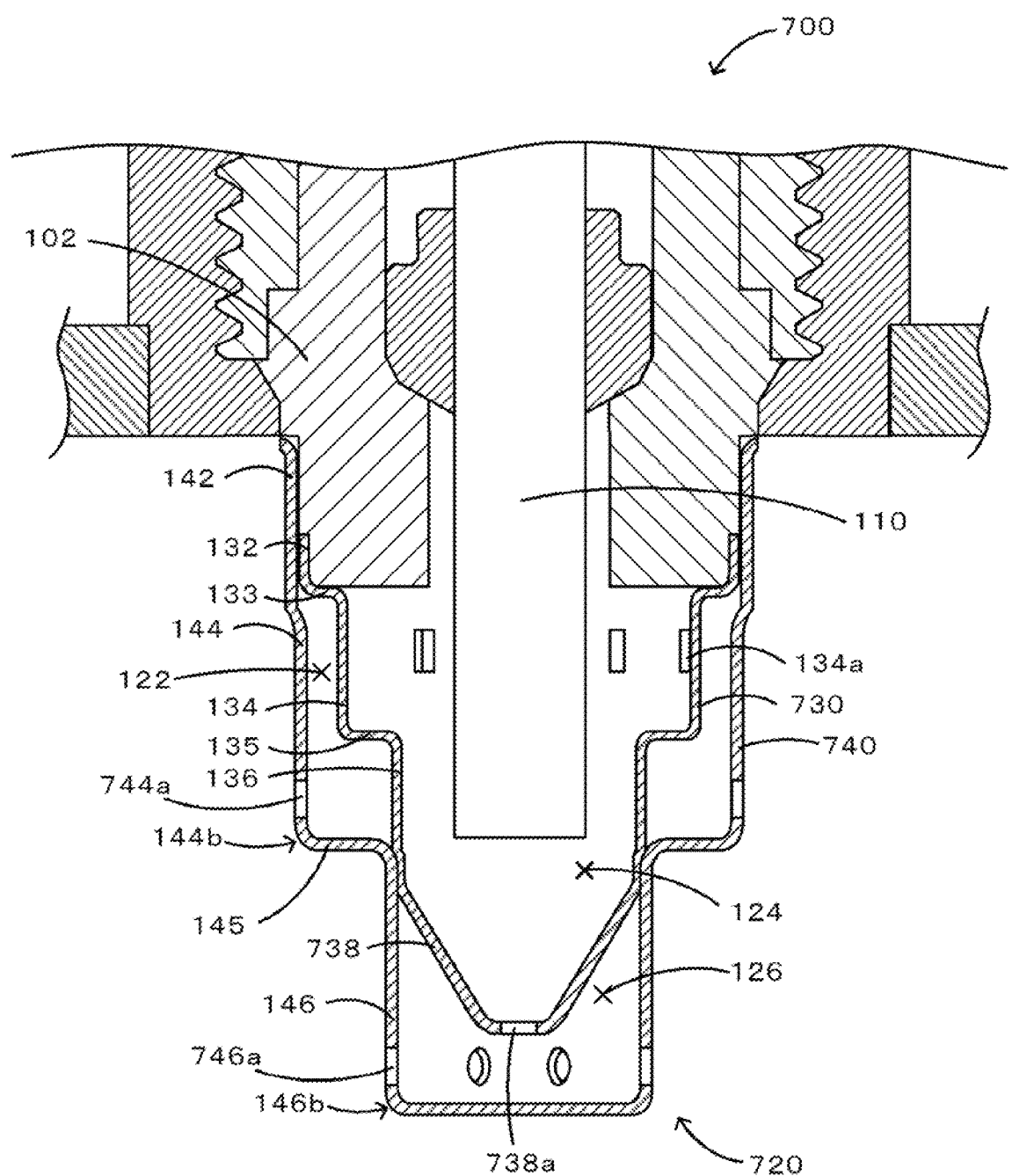
FIG. 18 is a vertical sectional view of the structure of a gas concentration detection sensor 700 in Comparative Examples 3 to 5.

A plurality of gas concentration detection sensors 700 shown in FIG. 18 were fabricated. Each gas concentration detection sensor 700 included, as a protective cover 720, an inner protection cover 730 and an outer protection cover 740. The inner protection cover 730 had the same structure as the inner protection cover 130 in FIG. 2, except for the difference in shape between an edge section 738 and the edge section 138 and that between a gas passing aperture 738a and each gas passing aperture 138a and except for omission of the step element 137. The components except the edge section 738 and the gas passing aperture 738a are designated by the same reference numerals without duplicated explanation. Unlike the edge section 138, the edge section 738 was shaped in an inverted triangular frustum. The inner diameter of part of the edge section connecting to the stem section 136 was 7.4 mm and the diameter of a bottom face of the edge section 738 was 2.4 mm. The gas passing aperture 738a was a circular hole located at the central point of the bottom face of the edge section 738 and the inner diameter thereof was 1 mm. The outer opening plane of the gas passing aperture 738a formed an angle of 0 degree with the bottom face of the edge section 738. The outer protection cover 740 had the same structure as the outer protection cover 140 in FIG. 2, except for first outer gas apertures 744a and second outer gas apertures 746a. The components except the first outer gas apertures 744a and the second outer gas apertures 746a are designated by the same reference numerals without duplicated explanation. The first outer gas apertures 744a were located around the side face of the stem section 144 and the second outer gas apertures 746a were located around the side face of the edge section 146. The gas concentration detection sensors were fabricated such that the inner diameter φ1 of each first outer gas aperture 744a and the inner diameter φ2 of each second outer gas aperture 746a of the outer protection cover 710 were variously changed as shown as Comparative Examples 1 to 3 in Table 1. Six first outer gas apertures 744a were arranged at equal intervals and six second outer gas apertures 746a were arranged at equal intervals similar to Examples 1 to 2.

Comparative Example 6

Figure 19:
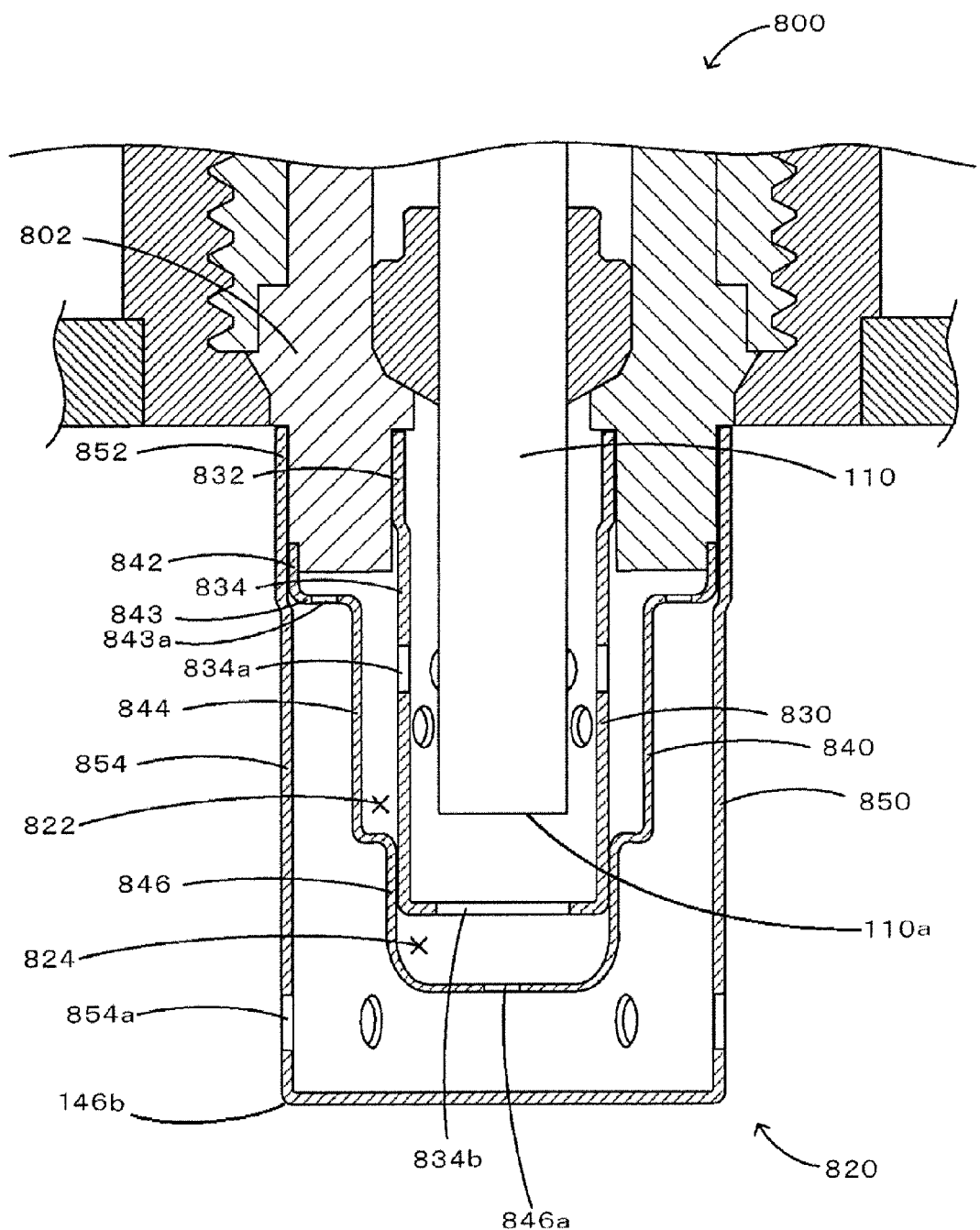
FIG. 19 is a vertical sectional view of the structure of a gas concentration detection sensor 800 in Comparative Example 6.
Figure 20:
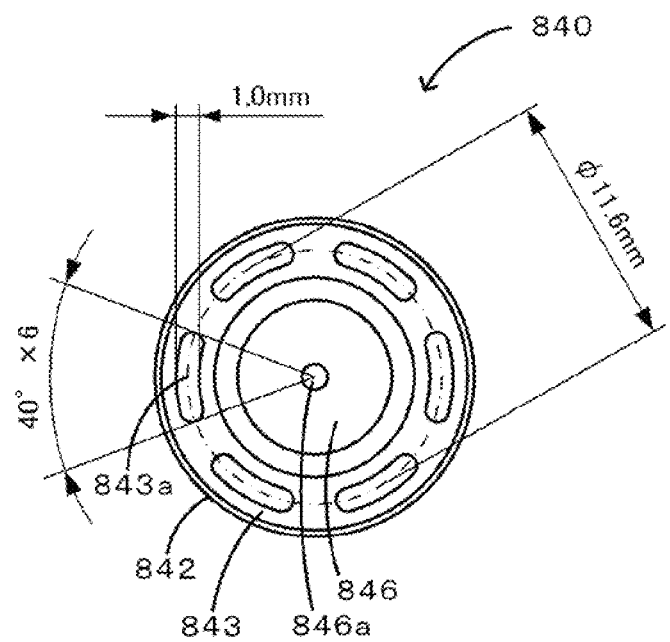
FIG. 20 is a plan view (top view) of an intermediate protection cover 840.

A gas concentration detection sensor 800 shown in FIG. 19 was fabricated. The gas concentration detection sensor 800 included a protective cover 620 having a triple-layered structure, namely, including an inner protection cover 830 covering ever the free end of the sensor element 110 and having a thickness of 0.3 mm, an intermediate protection cover 840 covering over the inner protection cover 830 and having a thickness of 0.3 mm, and an outer protection cover 850 covering over the intermediate protection cover 840 and having a thickness of 0.4 mm. The inner protection cover 830 had an outer circumferential face that was in contact with a metal main clamp 802 and included a cylindrical large-diameter section 832 having an axial length of 5.5 mm and an inner diameter of 6.8 mm and a bottomed cylindrical edge section 834 having an axial length of 13.9 mm and an inner diameter of 6.4 mm. Twelve inner gas apertures 834a each having an inner diameter of 1.5 mm were arranged around a side face of the edge section 834. A gas passing aperture 834h having an inner diameter of 5 mm was disposed at the center of a bottom face of the edge section 834. The outer opening plane of the gas passing aperture 834b formed an angle of 0 degree with the bottom face of the edge section 834. The inner gas apertures 834a were arranged at equal intervals such that they were axially (vertically in FIG. 19) staggered in two levels. The intermediate protection cover 840 had an inner circumferential face that was in contact with the metal main clamp 802 and included a large-diameter section 842 having an axial length of 1.6 mm and an inner diameter of 13.5 mm, a cylindrical stem section 844 having an axial length of 8.4 mm and an inner diameter of 9.1 mm, and a bottomed cylindrical edge section 846 having an axial length of 5.5 mm and an inner diameter of 6.9 mm. The large-diameter section 842 was connected to the stem section 844 through a step element 843. The stem section 844 was also connected to the edge section 846 through a step. In the step element 843, as shown in FIG. 20, six first intermediate gas apertures 843a, each shaped in a 40-degree arc of a circle having a diameter of 11.6 mm and each having a width of 1 mm, were arranged at equal intervals. A second intermediate gas aperture 846a having an inner diameter of 1.1 mm was formed at the center of a bottom face of the edge section 846. The outer protection cover 850 had an inner circumferential face that was in contact with the metal main clamp 802 and included a cylindrical large-diameter section 852 having an axial length of 5.6 mm and an inner diameter of 14.4 mm and a bottomed cylindrical edge section 854 having an axial length of 18.2 mm and an inner diameter of 13.8 mm. Six outer gas apertures 854a each having an inner diameter of 2 mm were formed around a side face of the edge section 854. The edge section 834 of the inner protection cover 830 was in contact with the edge section 846 of the intermediate protection cover 840, such that a space defined by the inner protection cover 830 and the intermediate protection cover 840 was divided into an upper chamber 822 and a lower chamber 824.

Comparative Example 7

Figure 21:
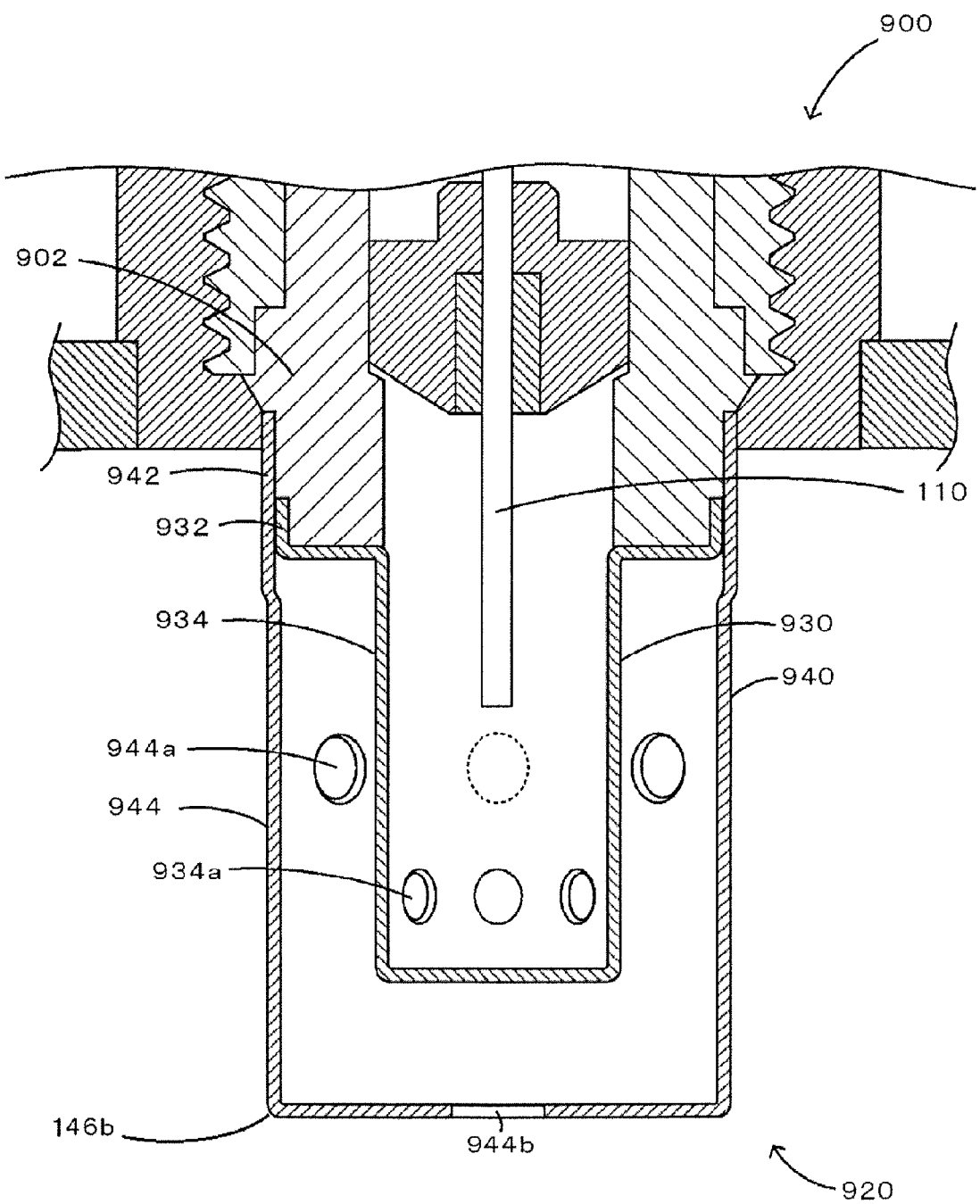
FIG. 21 is a vertical sectional view of the structure of a gas concentration detection sensor 900 in Comparative Example 7.

A gas concentration detection sensor 900 shown in FIG. 21 was fabricated. The gas concentration detection sensor 900 included a protective cover 920 having a double-layered structure, namely, including an inner protection cover 930 covering over the free end of the sensor element 110 and having a thickness of 0.3 mm and an outer protection cover 940 covering over the inner protection cover 930 and having a thickness of 0.4 mm. The inner protection cover 930 had an inner circumferential face that was in contact with a metal main clamp 902 and included a cylindrical large-diameter section 932 having an axial length of 1.5 mm and an inner diameter of 13.7 mm and a bottomed cylindrical edge section 934 having an axial length of 12.4 mm and an inner diameter of 6.9 mm. The large-diameter section 932 was connected to the edge section 934 through a step. Six inner gas apertures 934a each having an inner diameter of 1.5 mm were arranged at equal intervals around a side face of the edge section 934. The outer protection cover 940 had an inner circumferential face that was in contact with the metal main clamp 902 and included a cylindrical large-diameter section 942 having an axial length of 5.5 mm and an inner diameter of 14.4 mm and a bottomed cylindrical edge section 944 having an axial length of 15.3 mm and an inner diameter of 13.8 mm. Six first outer gas apertures 944a each having an inner diameter of 2 mm were arranged at equal intervals around a side face of the edge section 944. A second outer gas aperture 944b having an inner diameter of 3.8 mm was disposed at the center of a bottom face of the edge section 944.

Evaluation Test 1

The gas concentration detection sensors of Examples 1 to 8 and Comparative Examples 1 to 7 were evaluated with respect to sensor output responses and water adhesions of the sensor elements. The results are shown in Table 1 and FIG. 23. A method of examining the sensor output response and the water adhesion of each sensor element is as described below.

Sensor Output Response

Each gas concentration detection sensor was attached to the piping 200 as shown in FIG. 1. As regards the object gas, a reference gas controlled at an NO concentration of 70 ppm and a lambda value of 1.05 after burner combustion was supplied instead of an exhaust gas from an engine until a sensor output was stable. After that, oxygen was introduced into the reference gas through a gas introduction port to supply a gas mixture at an NO concentration of 70 ppm and a lambda value of 1.35 until the sensor output was stable. The sensor element 110 then functioned as an oxygen concentration cell to generate an electromotive force, such that the sensor output rose. Time t10 required between the time when oxygen was introduced into the reference gas and the time when the sensor output rose to 10% of a maximum value and time t90 required between the time when oxygen was introduced into the reference gas and the time when the sensor output rose to 90% of the maximum value were obtained. The difference Δt (=t90−t10) therebetween corresponds to response time (units:sec). The shorter the response time, the higher the response of the gas concentration detection sensor.

Water Adhesion of Sensor Element

Figure 22:
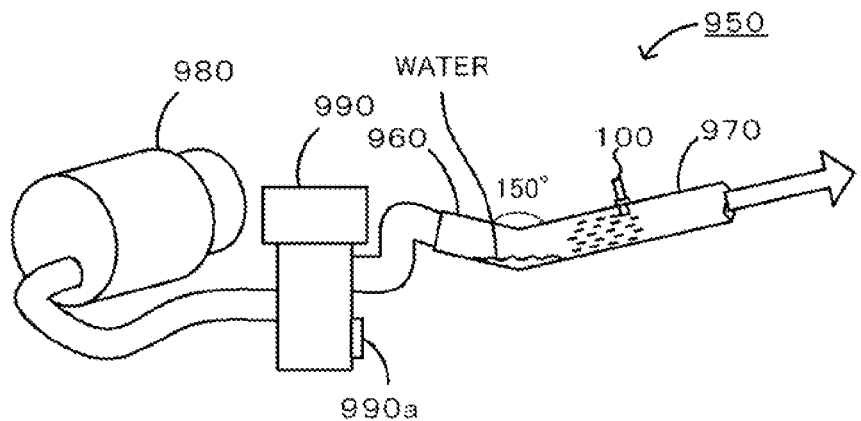
FIG. 22 is an explanatory view of a break water amount measuring device 950.

A water adhesion was obtained using a break water amount measuring device 950 shown in FIG. 22. The prepared break water amount measuring device 950 included two pipes 960 and 970 each having a diameter of 28 mm, a blower 980, a switching valve 990, and the gas concentration detection sensor 100 such that the pipes were joined to each other at an angle of 150 degrees, the blower 980 was positioned 300 mm apart from the joint and was connected to the pipe through the switching valve 990, and the gas concentration detection sensor 100 was disposed 400 mm apart from the joint on the opposite side of the joint from the blower 980. While an arbitrary amount of water was accumulated in the joint, the blower 980 was driven under predetermined driving conditions such that the air was blown from the blower 980 to the pipe 960. This blowing allowed the water in the joint to fly toward the sensor 100, thus discharging the whole of the accumulated water to the outside of the pipe 970. During that time, the presence or absence of an abnormal output of the sensor element 110 was determined. The same test was performed ten times with the same amount of water for each gas concentration detection sensor. It any abnormal output was not detected, the amount of water was increased by 10 cm$^3$ and the same test was performed ten times. The test was similarly repeated while the amount of water was increased by 10 cm$^3$ until an abnormal output was detected at least one time out of ten times. An initial amount of water in the tests during which an abnormal output was detected at least one time is referred to as an amount of water at break, or break water amount (units:liter). The inverse of the break water amount is referred to as a water adhesion (units:1/liter). As the water adhesion is lower, the adhesion of water to the sensor element 110 is more effectively prevented. The predetermined driving conditions for the blower were that after energizing the heater in the sensor element 110 was finished, the blower 980 produced a flow of air at an air velocity of about 75 m/s while the switching valve 990 shown in FIG. 16 was connected to a bypass 990a, and the switching valve was then switched to the pipe 960 to blow the air to the pipe 960 for three seconds.

TABLE 1

|  | Example Nos. |  |  |  |  |  |  |  | Comparative Example Nos. |  |  |  |  |  |  |
|---|---|---|---|---|---|---|---|---|---|---|---|---|---|---|---|
|  | 1 | 2 | 3 | 4 | 5 | 6 | 7 | 8 | 1 | 2 | 3 | 4 | 5 | 6 | 7 |
| Inner Diameter of First Outer Gas Aperture φ1(mm) | 1 | 1 | 0.8 | 0.8 | 0.8 | 1 | 1 | 1 | 1 | 1 | 1 | 1 | 1.5 | — | 2 |
| Number of First Outer Gas Aperture | 6 | 6 | 8 | 12 | 4 | 6 | 6 | 6 | 6 | 6 | 6 | 6 | 6 | — | 6 |
| Inner Diameter of Second Outer Gas Aperture φ2(mm) | 1 | 1.2 | 0.8 | 1.2 | 0.8 | 1 | 1 | 1.2 | 1 | 1 | 1.5 | 1 | 1.5 | — | 3.8 |
| Number of Second Outer Gas Aperture | 6 | 6 | 8 | 6 | 8 | 6 | 6 | 6 | 6 | 6 | 6 | 6 | 6 | — | 1 |
| Inner Diameter of Outer Gas Aperture (mm) | — | — | — | — | — | — | — | — | — | — | — | — | — | 2 | — |
| Number of Outer Gas Aperture | — | — | — | — | — | — | — | — | — | — | — | — | — | 6 | — |
| Inner Diameter Ratio φ2/φ1 | 1 | 1.2 | 1 | 1.5 | 1 | 1 | 1 | 1.2 | 1 | 1 | 1.5 | 1 | 1 | — | 1.9 |
| Angle of First and Second Outer Gas Aperture θ(°) | 45 | 45 | 45 | 45 | 45 | 10 | 80 | 45 | 5 | 85 | — | — | — | — | — |
| Area Ratio (Total area of 2nd Outer Gas Apertures/Total Area | 1.00 | 1.44 | 1.00 | 1.13 | 2.00 | 1.00 | 1.00 | 1.44 | 1.00 | 1.00 | 2.25 | 1.00 | 1.00 | — | 0.60 |

TABLE 1-continued

|  | Example Nos. | | | | | | | | Comparative Example Nos. | | | | | | |
| --- | --- | --- | --- | --- | --- | --- | --- | --- | --- | --- | --- | --- | --- | --- | --- |
|  | 1 | 2 | 3 | 4 | 5 | 6 | 7 | 8 | 1 | 2 | 3 | 4 | 5 | 6 | 7 |
| of 1st Outer Gas Apertures) | | | | | | | | | | | | | | | |
| Reaponse Time (sec) | 0.8 | 0.6 | 0.9 | 0.65 | 0.7 | 0.6 | 0.8 | 0.55 | 0.5 | 1 | 1.2 | 1.4 | 1 | 1.5 | 2 |
| Water Adhesion (1/L) | 3.33 | 2.86 | 3.33 | 2.86 | 2.50 | 5.00 | 5.00 | 3.33 | 8.33 | 6.67 | 6.67 | 8.33 | 11.11 | 7.69 | 7.14 |
| Angle of Gas Passing Aperture (°) | 90 | 90 | 90 | 90 | 90 | 90 | 90 | 45 | 90 | 90 | 0 | 0 | 0 | 0 | — |

Figure 23:
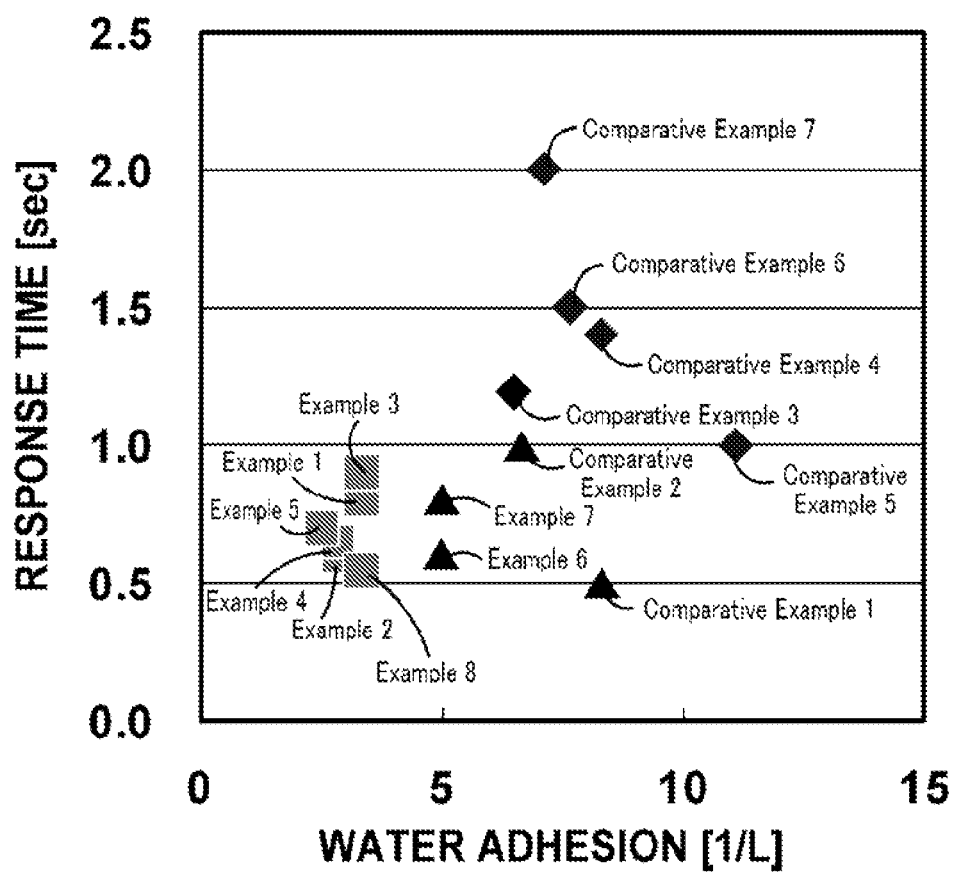
FIG. 23 is a graph showing the response time of each of gas concentration detection sensors of Examples 1 to 7 and Comparative Examples 1 to 8 plotted against the water adhesion thereof.

FIG. 23 is a graph showing the response time of each of the gas concentration detection sensors of Examples 1 to 8 and Comparative Examples 1 to 7 plotted against the water adhesion. Table 1 and FIG. 23 demonstrate that the response time of each of the sensors of Examples 1 to 8 is shorter than those of Comparative Examples 3 to 7 and the water adhesion thereof is lower than those of Comparative Examples 3 to 7. As regards Examples 2, 4, and 5 in which the total area of the second outer gas apertures 146a is larger than that of the first outer gas apertures 144a, the response time of each of the sensors of Examples 2, 4, and 5 is shorter than those of Examples 1 and 3 in which the total area of the second outer gas apertures 146a is equal to that of the first outer gas apertures 144a and the water adhesion thereof is lower than those of Examples 1 and 3. The response time of each of the sensors of Examples 1 to 8, in which the formed angle θ is in the range of 10 degrees to 80 degrees, is shorter than those of Examples 3 to 7 and the water adhesion thereof is lower than those of Examples 3 and 7. The response time of each of the sensors of Comparative Examples 1 and 2, in which the formed angle θ is not in the range of 10 degrees to 80 degrees, is shorter than that of the sensor of Comparative Example 3 but the water adhesion thereof is higher than that of Comparative Example 3.

As regards the comparison between Comparative Examples 3 and 4, the response time of the sensor of Comparative Example 3, in which the total area of the second outer gas apertures 346a is larger than that of the first outer gas apertures 344a, is shorter than that of Comparative Example 4 in which the total area of the second outer gas apertures 346a is equal to that of the first outer gas apertures 344a and the water adhesion thereof is lower than that of Comparative Example 4. Even when the first outer gas apertures and the second outer gas apertures are not arranged in the corners, therefore, the advantage of preventing water from adhering to the sensor element and the advantage of enhancing the gas concentration determination response may be ascribed to the fact that the total area of the second outer gas apertures is larger than that of the first outer gas apertures.

As regards the comparison between Examples 1 and 8, the water adhesion of the sensor of Example 8, in which the gas passing apertures are positioned in the boundary portion between the side face and the bottom face of the edge section of the inner protection cover and the angle formed by the outer opening plane of each gas passing aperture and the bottom face of the edge section is 45 degrees, is equal to the water adhesion of the sensor of Example 1 but the response time thereof is shorter than that of Example 1.

Evaluation Test 2

Figure 24:
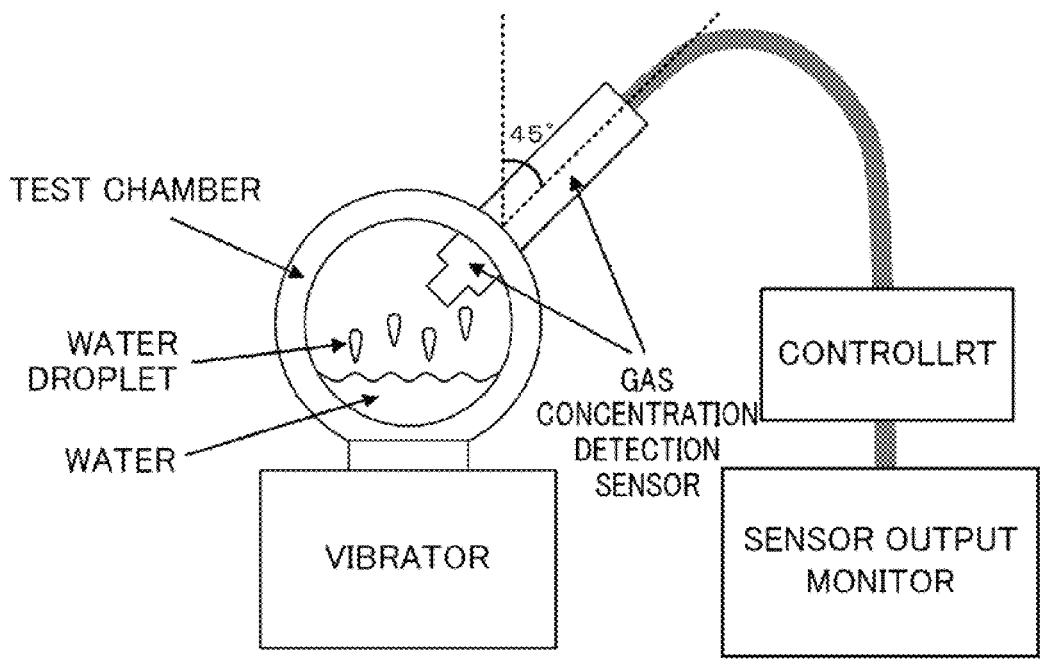
FIG. 24 is an explanatory view of a situation of a vibration test.

Each of the gas concentration detection sensors of Example 2 and Comparative Examples 4 and 7 underwent a vibration test simulating a phenomenon in which vibration causes water accumulated in piping to adhere to the sensor element during operation. FIG. 24 shows a situation of the vibration test. The vibration test was performed as described below. The gas concentration detection sensor was attached to a test chamber mounted on a vibrator such that the sensor was inclined at an angle of 45 degrees relative to the vertical direction. The gas concentration detection sensor was connected to a controller controlling a power output of the heater and a sensor output monitor for measuring a power control value of the heater. Subsequently, water was supplied into the test chamber and the vibrator vibrated the test chamber with a sinusoidal wave while varying a frequency in a range of 10 to 200 Hz. During vibration, the controller controlled the heater in the sensor element at 100° C. The sensor output monitor measured a power control value of the heater at that time. As the amount of water adhering to the sensor element is larger, the temperature of the sensor element is lower, so that the power control value becomes larger to increase a power output of the heater.

Figure 25:
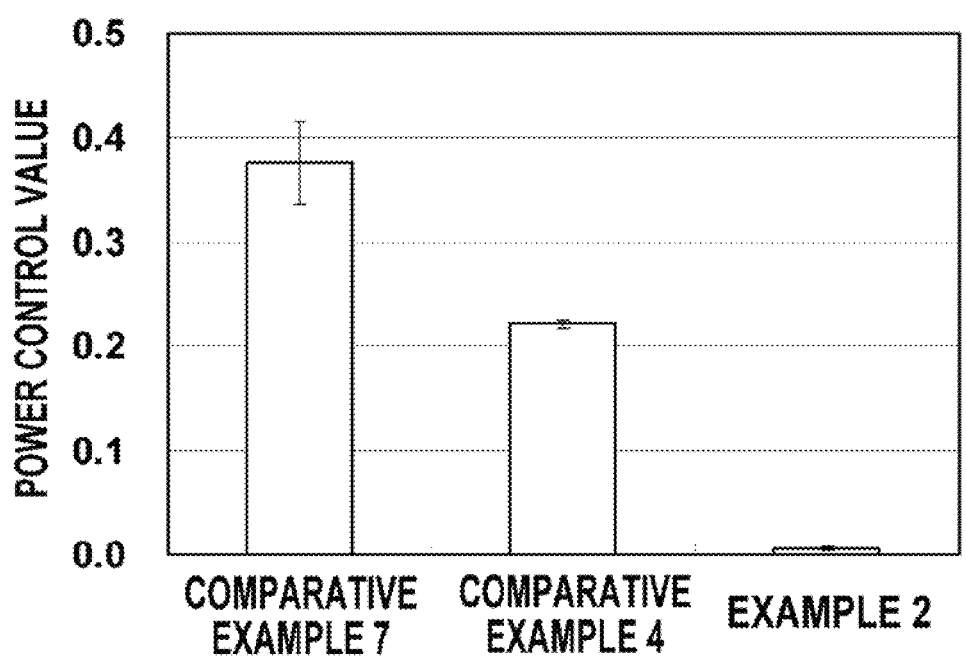
FIG. 25 is a graph showing vibration test results in Example 2 and Comparative Examples 4 and 7.

FIG. 25 shows results of Evaluation Test 2. FIG. 25 demonstrates that the power control value in Example 2 is lower than those of Comparative Examples 4 and 7. It was therefore confirmed that the lower water adhesion of the sensor element of the gas concentration detection sensor of Example 2 during vibration than Comparative Examples 4 and 1, in which the outer gas apertures were arranged on the side faces and the bottom faces of the outer protection covers, was ascribed to the arrangement of the first outer gas apertures and the second outer gas apertures in the boundary portion between the side face and the bottom face of the outer protection cover.

Evaluation Test 3

Each of the gas concentration detection sensors of Example 8 and Comparative Examples 4 and 7 underwent a drain test to observe the sensor changing from a state where water was previously accumulated in the cuter and inner protection covers to a state where the water was removed. This test was performed using the break water amount measuring device 950 shown in FIG. 22. Specifically, the gas concentration detection sensor was attached to the pipe 970 such that the sensor was inclined at an angle of 45 degrees relative to the vertical direction. The joint between the pipes 960 and 970 had no water. Instead, an arbitrary amount of water was previously injected into the outer and inner protection covers of the gas concentration detection sensor. The blower 980 was driven under predetermined driving conditions in this state such that the air was blown from the blower 980 to the pipe 960. The heater in the sensor element was controlled at 100° C. during blowing and a power control value at that time was measured. When water is injected into the inner protection cover and adheres to the sensor element, the temperature of the sensor element falls, so that the power control value becomes large to increase a power output of the heater. As blowing causes more amount water to be drained out of the inner protection cover, therefore, the power control value becomes lower.

Figure 26:
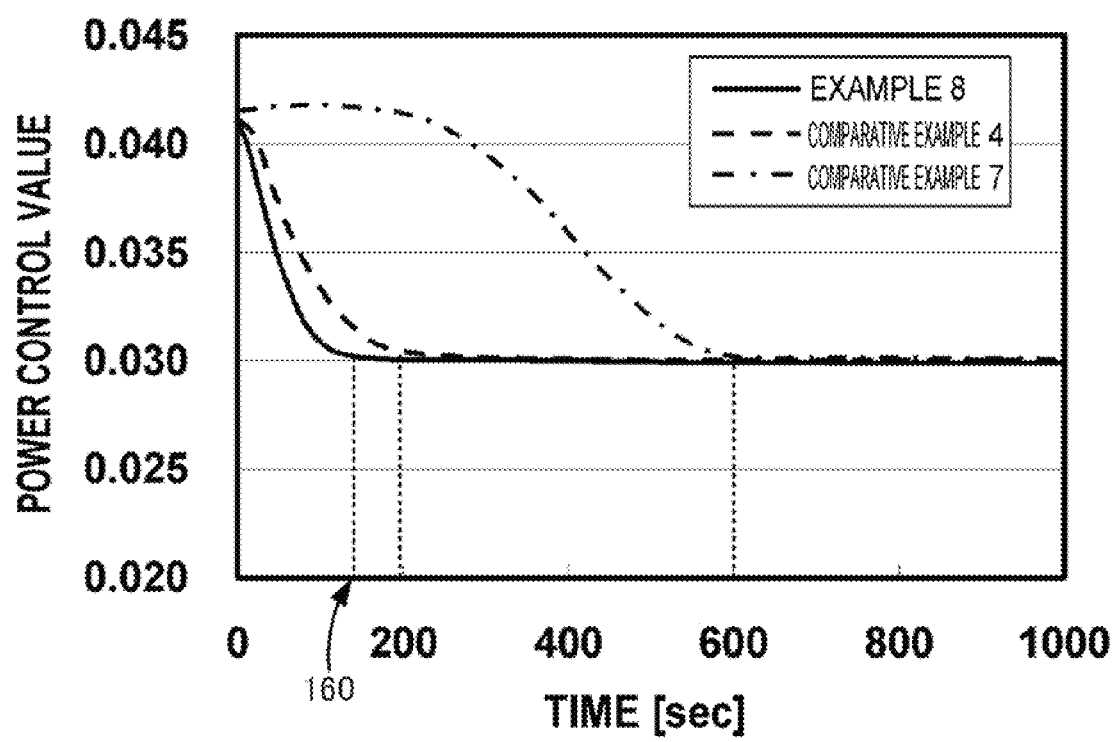
FIG. 26 is a graph showing drain test results in Example 8 and Comparative Examples 4 and 7.
Figure 27:
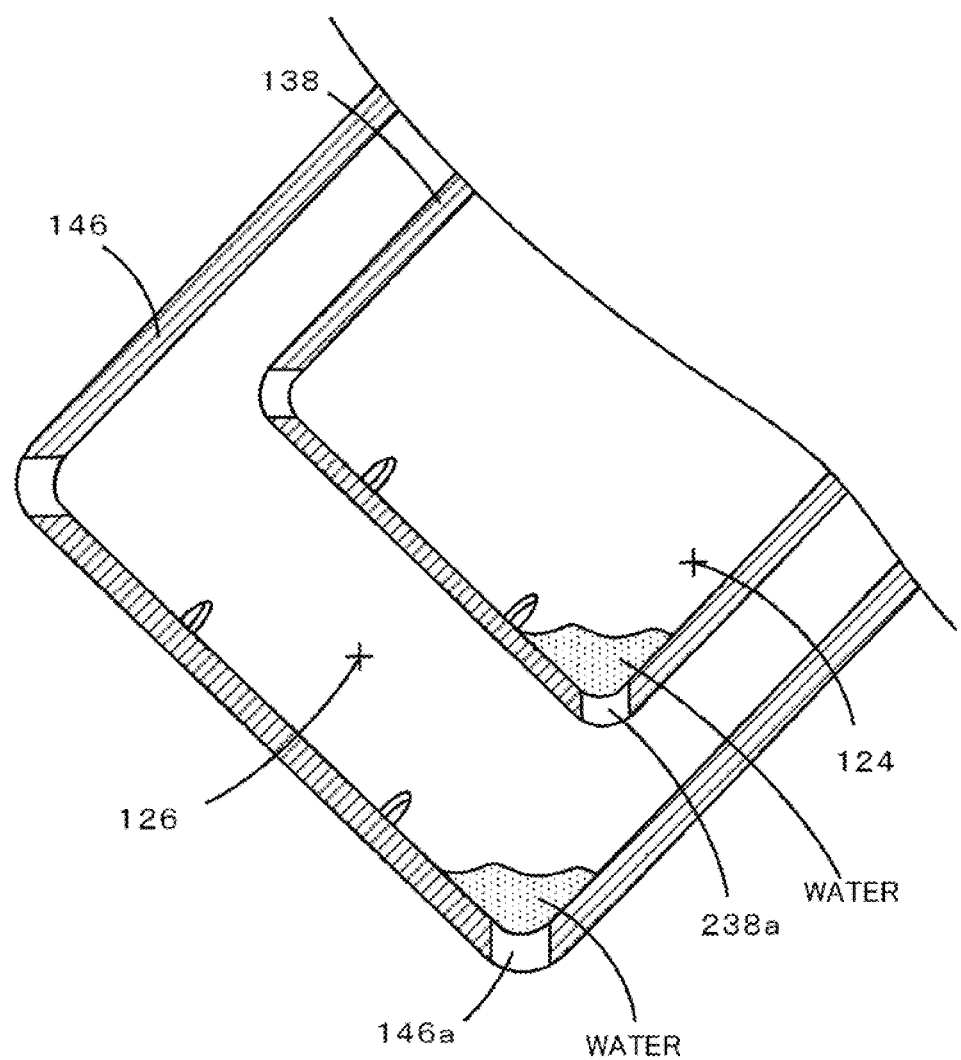
FIG. 27 is an explanatory view of the gas concentration detection sensor of Example 8 inclined at a 45 degree angle.

FIG. 26 shows results of Evaluation Test 3. As will be seen from FIG. 26, there is not much difference among power control values of Example 8 and Comparative Examples 4 and 7 measured at the start of blowing. In Example 8, the power control value sharply decreased in the 160th second after the start of blowing and was stable after the 160th second. It took 200 seconds in Comparative Example 4 and it took 600 seconds in Comparative Example 7 until the power control value was stable. This proved that the gas concentration detection sensor of Example 8 lowers the probability that water enters the protective cover and adheres to the sensor element, compared with Comparative Examples 4 and 7 and, furthermore, even if water enters the inner protection cover, the water tends to be drained (water drainability is high) in Example 8. It is thought that water tends to be drained outside from the outer protection cover 140 in the gas concentration detection sensor of Example 8 because the first outer gas apertures 146a are located in the first corner 144a and the second outer gas apertures 146a are located in the second corner 146b. Also, it is thought that water tends to be drained outside from the inner protection cover 130 in the gas concentration detection sensor of Example 8 because the gas passing aperture 238a is located in the boundary portion between the side face and the bottom face of the inner protection cover 130. In the state where the gas concentration detection sensor of Example 8 is inclined at a 45 degree angle as shown in FIG. 27, the second outer gas apertures 146a come to the lowermost position of the second gas chamber 126 and the gas passing apertures 238a come to the lowermost position of the sensor element chamber 124. Therefore, water in the second gas chamber 126 tends to be drained through the second outer gas apertures 116a in Example 8, thus preventing pooling of water as illustrated in FIG. 27, compared with Comparative Examples 4 and 7 in which the second outer gas apertures 146a are not located in the second corner 146b. Similarly, water in the inner protection cover 130 tends to be drained through the passing apertures 238a in Example 8, thus preventing pooling of water as illustrated in FIG. 27, compared with Comparative Examples 4 and 7 in which the gas passing apertures 238a are not located in the boundary portion between the side face and the bottom face of the inner protection cover 130. Though not illustrated, similarly, water in the first gas chamber 122 tends to be drained through the first outer gas apertures 144a in Examples 6, thus preventing pooling of water, compared with Comparative Examples 4 and 7. Compared with Comparative Examples 4 and 7, the advantages of this high drainability and prevention of water pooling are obtained similarly in Example 8 when the gas concentration detection sensor is inclined at an angle of 0 to 90 degrees, even if not 45 degrees. In a cold region or during winter season, condensation may occur in a protection cover of a gas concentration detection sensor attached to an engine exhaust path. When an engine starts in such a state, water formed by condensation may adhere to a sensor element, thus causing cracking. Since the structure of the gas concentration detection sensor of Example 8 facilitates the draining of the water in such a case, the structure may lower the probability that cracking occurs, compared with Comparative Examples 4 and 7.

The present application claims priorities from Japanese Patent Application No. 2010-114527 filed on May 18, 2010, and Japanese Patent Application No. 2011-109373 filed on May 16, 2011, the entire contents of both of which are incorporated herein by reference.

What is claimed is:

1. A gas concentration detection sensor comprising:
    a sensor element that detects a concentration of a selected gas included in an object gas;
    a bottomed cylindrical inner protection cover that covers over a free end of the sensor element;
    an outer protection cover having a side face and a bottom face;
    a plurality of outer gas apertures arranged in a boundary portion between the side face and the bottom face of the outer protection cover; and
    an inner gas aperture positioned closer to a base end of the sensor element than the outer gas apertures, the inner gas aperture allowing the object gas to flow inside and outside the inner protection cover,
    wherein an angle formed by the outer opening plane of each outer gas aperture and the bottom face of the outer protection cover is in a range of 10 degrees to 80 degrees.

2. The gas concentration detection sensor according to claim 1, wherein the outer protection cover has a cylindrical stem section, a bottomed cylindrical edge section having a smaller diameter than a diameter of the stem section, and a step element connecting the stem section with the edge section,
    the outer gas apertures include a plurality of first outer gas apertures arranged in a first corner, serving as a boundary portion between a side face of the stem section of the outer protection cover and a bottom face of the step element of the outer protection cover, and a plurality of second outer gas apertures arranged in a second corner, serving as a boundary portion between a side face and a bottom face of the edge section of the outer protection cover,
    the inner gas aperture is positioned closer to the base end of the sensor element than the first outer gas apertures, and the sensor further includes
    a first gas chamber defined by the stem section and the step element of the outer protection cover and the inner protection cover such that the first gas chamber communicates with the inside of the inner protection cover through the inner gas aperture,
    a second gas chamber defined by the edge section of the outer protection cover and the inner protection cover such that the second gas chamber does not directly communicate with the first gas chamber, and
    a gas passing aperture that allows the object gas to flow between the second gas chamber and the inside of the inner protection cover.

3. The gas concentration detection sensor according to claim 2, wherein the total area of openings of the second outer gas apertures is larger than that of the first outer gas apertures.

4. The gas concentration detection sensor according to claim 3, wherein the gas passing aperture is disposed in a position other than extensions of the second outer gas apertures.

5. The gas concentration detection sensor according to claim 3, wherein the first outer gas apertures have the same area of opening,
    the second outer gas apertures have the same area of opening, and
    the area of opening of each second outer gas aperture is equal to or larger than that of each first outer gas aperture.

6. The gas concentration detection sensor according to claim 2, wherein the first outer gas apertures are three or more apertures arranged at equal intervals, and
    the second outer gas apertures are three or more apertures arranged at equal intervals.

7. The gas concentration detection sensor according to claim 2, wherein the gas passing aperture is disposed in a boundary portion between a side face and a bottom face of the inner protection cover, and an angle formed by the outer opening plane of the gas passing aperture and the bottom face of the inner protection cover is in a range of 10 degrees to 80 degrees.

* * * * *